US008822213B2

(12) United States Patent
Stayton et al.

(10) Patent No.: US 8,822,213 B2
(45) Date of Patent: Sep. 2, 2014

(54) BISPECIFIC INTRACELLULAR DELIVERY VEHICLES

(75) Inventors: Patrick S. Stayton, Seattle, WA (US); Allan S. Hoffman, Seattle, WA (US); Anthony J. Convertine, Seattle, WA (US); Craig L. Duvall, Nashville, TN (US); Robert W. Overell, Seattle, WA (US); Paul H. Johnson, Snohomish, WA (US)

(73) Assignees: University of Washington, Seattle, WA (US); PhaseRx, Inc., Seattle, WA (US)

( * ) Notice: Subject to any disclaimer, the term of this patent is extended or adjusted under 35 U.S.C. 154(b) by 67 days.

(21) Appl. No.: 13/127,968

(22) PCT Filed: May 13, 2009

(86) PCT No.: PCT/US2009/043852
§ 371 (c)(1),
(2), (4) Date: Jul. 27, 2011

(87) PCT Pub. No.: WO2010/053596
PCT Pub. Date: May 14, 2010

(65) Prior Publication Data
US 2011/0281354 A1 Nov. 17, 2011

Related U.S. Application Data

(60) Provisional application No. 61/171,381, filed on Apr. 21, 2009, provisional application No. 61/140,779, filed on Dec. 24, 2008, provisional application No. 61/140,774, filed on Dec. 24, 2008, provisional application No. 61/112,054, filed on Nov. 6, 2008, provisional application No. 61/112,048, filed on Nov. 6, 2008.

(51) Int. Cl.
*C12N 5/00* (2006.01)
*C12N 5/07* (2010.01)
*A61K 47/48* (2006.01)
*C07K 16/46* (2006.01)
*C07K 16/32* (2006.01)
*C07K 16/28* (2006.01)
*C07K 16/18* (2006.01)

(52) U.S. Cl.
CPC ....... *C07K 16/2881* (2013.01); *A61K 47/48507* (2013.01); *C07K 2317/31* (2013.01); *C07K 16/468* (2013.01); *C07K 16/32* (2013.01); *A61K 47/48561* (2013.01); *C07K 2317/622* (2013.01); *A61K 47/48176* (2013.01); *C07K 2319/10* (2013.01); *A61K 47/48715* (2013.01); *A61K 47/48246* (2013.01); *C07K 16/18* (2013.01)
USPC ............................ 435/325; 435/332; 435/328

(58) Field of Classification Search
USPC .......................................... 435/325, 328, 332
See application file for complete search history.

(56) References Cited

U.S. PATENT DOCUMENTS

| 4,699,784 A | 10/1987 | Shih |
| 5,057,313 A | 10/1991 | Shih |
| 6,359,054 B1 | 3/2002 | Lemieux |
| 6,383,811 B2 | 5/2002 | Wolff |
| 6,410,057 B1 | 6/2002 | Kweon-Choi |
| 6,780,428 B2 | 8/2004 | Ranger |
| 6,835,393 B2 | 12/2004 | Hoffman |
| 6,919,091 B2 | 7/2005 | Trubetskoy |
| 6,939,564 B2 | 9/2005 | Ranger |
| 7,033,607 B2 | 4/2006 | Trubetskoy |
| 7,094,810 B2 | 8/2006 | Sant |
| 7,098,032 B2 | 8/2006 | Trubetskoy |
| 7,217,776 B1 | 5/2007 | Mallapragada |
| 7,374,778 B2 | 5/2008 | Hoffman |
| 7,510,731 B2 | 3/2009 | Ranger |
| 7,524,680 B2 | 4/2009 | Wolff |
| 7,718,193 B2 | 5/2010 | Stayton |
| 7,737,108 B1 | 6/2010 | Hoffman |
| 7,901,920 B2 * | 3/2011 | Huckriede et al. ............ 435/236 |
| 8,367,113 B2 | 2/2013 | Gu |
| 2001/0007666 A1 | 7/2001 | Hoffman |
| 2003/0134420 A1 | 7/2003 | Lollo |
| 2003/0191081 A1 | 10/2003 | Lemieux |
| 2003/0211167 A1 | 11/2003 | Gustavsson |
| 2004/0072784 A1 | 4/2004 | Sant |
| 2004/0151775 A1 | 8/2004 | Rozema |

(Continued)

FOREIGN PATENT DOCUMENTS

| EP | 0 321 233 A1 | 6/1989 |
| EP | 2 180 004 A1 | 4/2010 |
| FR | 2 767 829 A1 | 3/1999 |
| WO | 99/29303 A1 | 6/1999 |
| WO | 01/87227 A2 | 11/2001 |
| WO | 03/087188 A1 | 10/2003 |
| WO | 2005/108614 A2 | 11/2005 |
| WO | 2006/016166 A1 | 2/2006 |
| WO | 2007/008300 A2 | 1/2007 |
| WO | 2007/109584 A1 | 9/2007 |

(Continued)

OTHER PUBLICATIONS

Kielian et al. (pH-Induced Alterations in the Fusogenic Spike Protein of Semliki Forest Virus. Journal of Cell Biology. 1985. 101:2284-2291).*

(Continued)

*Primary Examiner* — Karen Cochrane Carlson
*Assistant Examiner* — Natalie Moss
(74) *Attorney, Agent, or Firm* — Christensen O'Connor Johnson Kindness PLLC

(57) ABSTRACT

A composition for delivering an agent to a cell, comprising a bispecific affinity reagent and a pH-responsive, membrane destabilizing polymer. The bispecific affinity reagent may include a first affinity reagent covalently linked to a second affinity reagent, wherein the first affinity reagent binds to a molecule on the surface of a cell, and the second affinity reagent binds to an intracellular target.

23 Claims, 6 Drawing Sheets

(56) References Cited

U.S. PATENT DOCUMENTS

| | | |
|---|---|---|
| 2004/0162235 A1 | 8/2004 | Trubetskoy |
| 2005/0220880 A1 | 10/2005 | Lewis |
| 2005/0260276 A1 | 11/2005 | Yang |
| 2006/0134221 A1 | 6/2006 | Geall |
| 2006/0165810 A1 | 7/2006 | Discher |
| 2006/0171980 A1 | 8/2006 | Helmus |
| 2006/0235161 A1 | 10/2006 | Heller |
| 2007/0003609 A1 | 1/2007 | Collin-Djangone |
| 2007/0010632 A1 | 1/2007 | Kaplan |
| 2007/0037891 A1 | 2/2007 | Esfand |
| 2007/0059271 A1 | 3/2007 | Kataoka |
| 2007/0110709 A1 | 5/2007 | Ranger |
| 2007/0224241 A1 | 9/2007 | Stayton |
| 2008/0069902 A1 | 3/2008 | Zhao |
| 2008/0081075 A1 | 4/2008 | Hsiue |
| 2008/0171067 A1 | 7/2008 | Govindan |
| 2008/0243049 A1 | 10/2008 | Hardy |
| 2009/0036625 A1 | 2/2009 | Chang |
| 2010/0150952 A1 | 6/2010 | Stayton |

FOREIGN PATENT DOCUMENTS

| | | |
|---|---|---|
| WO | 2008/004978 A1 | 1/2008 |
| WO | 2008/022309 A2 | 2/2008 |
| WO | 2008/071009 A1 | 6/2008 |
| WO | 2008/085556 A2 | 7/2008 |
| WO | 2008/148174 A1 | 12/2008 |
| WO | 2008/153940 A1 | 12/2008 |
| WO | 2009/009025 A1 | 1/2009 |
| WO | 2009/021728 A2 | 2/2009 |
| WO | 2009/140421 A2 | 11/2009 |
| WO | 2009/140423 A2 | 11/2009 |
| WO | 2009/140427 A2 | 11/2009 |
| WO | 2009/140429 A2 | 11/2009 |
| WO | 2009/140432 A2 | 11/2009 |
| WO | 2010/021770 A1 | 2/2010 |
| WO | 2010/053596 A1 | 5/2010 |
| WO | 2010/053597 A2 | 5/2010 |
| WO | 2010/054266 A2 | 5/2010 |
| WO | 2010/077678 A2 | 7/2010 |

OTHER PUBLICATIONS

Kielian et al. (pH-Induced Alterations in the Fusogenic Spike Protein of Semliki Forest Virus. Journal of Cell Biology 1985.101:2284-2291).*

Lackey et al. A Biomimetic pH-Responsive Polymer Directs Endosomal Release and Intracellular Delivery of an Endocytosed Antibody Complex. Bioconjugate Chem. 13, 996-1001.*

International Search Report and Written Opinion, mailed Feb. 9, 2010, issued in corresponding International Application No. PCT/US2009/043852, filed May 13, 2009, 9 pages.

Benoit, D.S.W., et al., "Resensitizing Multidrug Resistant Cells to Doxorubicin Through plk1 Knockdown Using a Novel pH-Responsive Micelle siRNA Delivery System," Abstracts of Society for Biomaterials Meeting, Apr. 22, 2009, 1 page.

Bulmus, V., et al., "A New pH-Responsive and Glutathione-Reactive, Endosomal Membrane-Disruptive Polymeric Carrier for Intracellular Delivery of Biomolecular Drugs," Journal of Controlled Release 93(2):105-120, Dec. 2003.

Dufresne, M.-H., et al., "Characterization of Polyion Complex Micelles Designed to Address the Challenges of Oligonucleotide Delivery," Pharmaceutical Research 25(9):2083-2093, Sep. 2008.

Duvall, C.L., et al., "Polymer Enhanced Intracellular Delivery of a Pro-Apoptotic Peptide for Cancer Therapy," Abstracts of Society for Biomaterials Meeting, Apr. 22, 2009, 1 page.

El-Sayed, M.E.H., et al., "Rational Design of Composition and Activity Correlations for pH-Sensitive and Glutathione-Reactive Polymer Therapeutics," Journal of Controlled Release 101(1-3):47-58, Jan. 2005.

El-Sayed, M.E.H., et al., "Smart Polymeric Carriers for Enhanced Intracellular Delivery of Therapeutic Macromolecules," Expert Opinion on Biological Therapy 5(1):23-32, Jan. 2005.

Funhoff, A.M., et al., "Endosomal Escape of Polymeric Gene Delivery Complexes Is Not Always Enhanced by Polymers Buffering at Low pH," Biomacromolecules 5(1):32-39, Jan.-Feb. 2004.

Gaucher, G., et al., "Block Copolymer Micelles: Preparation, Characterization and Application in Drug Delivery," Journal of Controlled Release 109(1-3):169-188, Dec. 2005.

Henry, S.M., et al., "pH-Responsive Poly(styrene-alt-maleic anhydride) Alkylamide Copolymers for Intracellular Drug Delivery," Biomacromolecules 7(8):2407-2414, Aug. 2006.

Heredia, K.L., et al., "Reversible siRNA-Polymer Conjugates by RAFT Polymerization," Chemical Communications 28(28):3245-3247, Jul. 2008.

Inoue, T., et al., "An AB Block Copolymer of Oligo(methyl methacrylate) and Poly(acrylic acid) for Micellar Delivery of Hydrophobic Drugs," Journal of Controlled Release 51(2-3):221-229, Feb. 1998.

Jensen, K.D., et al., "Antisense Oligonucleotides Delivered to the Lysosome Escape and Actively Inhibit the Hepatitis B Virus," Bioconjucate Chemistry 13(5):975-984, Sep.-Oct. 2002.

Jeong, J.H., et al., "siRNA Conjugate Delivery Systems," Bioconjugate Chemistry 20(1):5-14, Jan. 2009.

Kataoka, K., et al., "Smart Polymeric Micelles as Nanocarriers for Oligonucleotides and siRNA Delivery," Nucleic Acids Symposium Series 49(1):17-18, Sep. 2005.

Kulkarni, S., et al, "Controlling the Aggregation of Conjugates of Streptavidin With Smart Block Copolymers Prepared Via the RAFT Copolymerization Technique," Biomacromolecules 7(10):2736-2741, Oct. 2006.

Meyer, M., et al., "Synthesis and Biological Evaluation of a Bioresponsive and Endosomolytic siRNA-Polymer Conjugate," Molecular Pharmaceutics 6(3):752-762, May-Jun. 2009.

Murthy, N., et al., "Bioinspired pH-Responsive Polymers for the Intracellular Delivery of Biomolecular Drugs," Bioconjugate Chemistry 14(2):412-419, Mar.-Apr. 2003.

Murthy, N., et al., "The Design and Synthesis of Polymers for Eukaryotic Membrane Disruption," Journal of Controlled Release 61(1-2):137-143, Aug. 1999.

Oishi M., et al., "Lactosylated Poly(ethylene glycol)-siRNA Conjugate Through Acid-Labile β-Thiopropionate Linkage to Construct pH-Sensitive Polyion Complex Micelles Achieving Enhanced Gene Silencing in Hepatoma Cells," Journal of the American Chemical Society 127(6):1624-1625, Feb. 2005.

Peppas, N.A., "Is There a Future in Glucose-Sensitive, Responsive Insulin Delivery Systems?" Drug Delivery Science and Technology 14(4):247-256, Sep. 2004.

Read, M.L., et al., "Physicochemical and Biological Characterisation of an Antisense Oligonucleotide Targeted Against the bcl-2 mRNA Complexed With Cationic-Hydrophilic Copolymers," European Journal of Pharmaceutical Sciences 10(3):169-177, May 2000.

Segura, T., and J.A. Hubbell, "Synthesis and In Vitro Characterization of an ABC Triblock Copolymer for siRNA Delivery," Bioconjugate Chemistry 18(3):736-745, May 2007.

Stayton, P.S., and A.S. Hoffman, "'Smart' pH-Responsive Carriers for Intracellular Delivery of Biomolecular Drugs," in V. Torchilin (ed.), "Fundamental Biomedical Technologies: Multifunctional Pharmaceutical Nanocarriers," Springer Science+Business Media, LLC, New York, May 2008, vol. 4, pp. 143-159.

Stayton, P.S., et al., "Intelligent Biohybrid Materials for Therapeutic and Imaging Agent Delivery," Proceedings of the IEEE 93(4):726-736, Apr. 2005.

Torchilin, V.P., "Micellar Nanocarriers: Pharmaceutical Perspectives," Pharmaceutical Research 24(1):1-16, Jan. 2007.

Wang, L., et al., "Delivery of Antisense Oligonucleotides Using HPMA Polymer: Synthesis of a Thiol Polymer and Its Conjugation to Water-Soluble Molecules," Bioconjugate Chemistry 9(6):749-757, Nov.-Dec. 1998.

Yamamoto, S.-I., et al., "Temperature- and pH-Responsive Dense Copolymer Brushes Prepared by ATRP," Macromolecules 41(19):7013-7020, Oct. 2008.

Yessine, M.-A., et al., "Proton-Actuated Membrane-Destabilizing Polyion Complex Micelles," Bioconjugate Chemistry 18(3):1010-1014, May-Jun. 2007.

(56) References Cited

OTHER PUBLICATIONS

Fishbein, I., et al., "Local Delivery of Gene Vectors From Bare-Metal Stents by Use of a Biodegradable Synthetic Complex Inihibits In-Stent Restenosis in Rat Carotid Arteries," Circulation 117(16):2096-2103, Apr. 2008.

Invitiation to Pay Additional Fees and Partial International Search Report mailed Apr. 26, 2011, issued in corresponding International Application No. PCT/US2010/056993, filed Nov. 17, 2010, 6 pages.

Varghese, O.P., et al., "In Situ Cross-Linkable High Molecular Weight Hyaluronan-Bisphosphonate Conjugate for Localized Delivery and Cell-Specific Targeting: A Hydrogel Linked Prodrug Approach," Journal of the American Chemical Society 131(25):8781-8783, Jul. 2009.

Cho, Y.W., et al., "Polycation Gene Delivery Systems: Escape From Endosomes to Cytosol," Journal of Pharmacy and Pharmacology 55(6):721-734, Jun. 2003.

Convertine, A.J., et al., "Development of a Novel Endosomolytic Diblock Copolymer for siRNA Delivery," Journal of Controlled Release 133(3):221-229, Feb. 2009.

International Search Report and Written Opinion mailed Mar. 7, 2011, issued in corresponding International Application No. PCT/US2010/056565, filed Nov. 12, 2010, 12 pages.

Oishi, M., et al., "Lactosylated Poly(ethylene glycol)-siRNA Conjugate Through Acid-Labile β-Thiopropionate Linkage to Construct pH-Sensitive Polyion Complex Micelles Achieving Enhanced Gene Silencing in Hepatoma Cells," Journal of the American Chemical Society 127(6):1624-1625, Feb. 2005.

Extended European Search Report mailed Feb. 5, 2014, issued in corresponding European Application No. 09 825 146.5, filed May 13, 2009, 9 pages.

Cheung, C.Y., et al., "A pH-Sensitive Polymer That Enhances Cationic Lipid-Mediated Gene Transfer," Bioconjugate Chemistry 12(6):906-910, Oct. 2001.

Hood, J.D., et al., "Tumor Regression by Targeted Gene Delivery to the Neovasculature," Science, New Series 296 (5577):2404-2407, Jun. 2002.

Jeong, Y.-I., et al., "Cellular Recognition of Paclitaxel-Loaded Polymeric Nanoparticles Composed of Poly(γ-benzyl L-glutamate) and Poly(ethylene glycol) Diblock Copolymer Endcapped With Galactose Moiety," International Journal of Pharmaceutics 296(2005):151-161, Apr. 2005.

Joralemon, M.J., et al., "Synthesis, Characterization, and Bioavailability of Mannosylated Shell Cross-Linked Nanoparticles," Biomacromolecules 5(3):903-913, May—Jun. 2004.

Kabanov, A.V., et al., "Pluronic Micelles as a Tool for Low-Molecular Compound Vector Delivery Into a Cell: Effect of *Staphylococcus-aureus* Enterotoxin B on Cell Loading With Micelle Incorporated Fluorescent Dye," Biochemistry International 26(6):1035-1042, May 1992.

Kyriakides, T.R., et al., "pH-Sensitive Polymers That Enhance Intracellular Drug Delivery In Vivo," Journal of Controlled Release 78(1-3):295-303, Jan. 2002.

Le Garrec, D., et al., "Micelles in Anticancer Drug Delivery," American Journal of Drug Delivery 2(1):15-42, Mar. 2004.

Lee, E.S., et al., "Super pH-Sensitive Multifunctional Polymeric Micelle," Nano Letters 5(2):325-329, Feb. 2005.

Nagasaki, Y. et al., "Sugar-Installed Block Copolymer Micelles: Their Preparation and Specific Interaction With Lectin Molecules," Biomacromolecules 2(4):1067-1070, Winter 2001.

Raso, V., "Intracellular Targeting Using Bispecific Antibodies," Methods in Molecular Medicine 25:37-49, Jan. 2000.

Sawant, R.M., et al., ""SMART" Drug Delivery Systems: Double-Targeted pH-Responsive Pharmaceutical Nanocarriers," Bioconjugate Chemistry 17:943-949, Jun. 2006.

Turk, M.J., et al., "Characterization of a Novel pH-Sensitive Peptide That Enhances Drug Release From Folate-Targeted Liposomes at Endosomal pHs," Biochimica et Biophysica Acta 1559(1):56-68, Feb. 2002.

Wakebayashi, D., et al., "Lactose-Conjugated Polyion Complex Micelles Incorporating Plasmid DNA as a Targetable Gene Vector System: Their Preparation and Gene Transfecting Efficiency Against Cultured HepG2 Cells," Journal of Controlled Release 95(3):653-664, Mar. 2004.

Yasugi, K., et al., "Sugar-Installed Polymer Micelles: Synthesis and Micellization of Poly(ethylene glycol)-Poly(D,L-lactide) Block Copolymers Having Sugar Groups at the PEG Chain End," Macromolecules 32:8024-8032, Nov. 1999.

Yoo, H.S., and T.G. Park, "Folate Receptor Targeted Biodegradable Polymeric Doxorubicin Micelles," Journal of Controlled Release 96(2):273-283, Apr. 2004.

\* cited by examiner

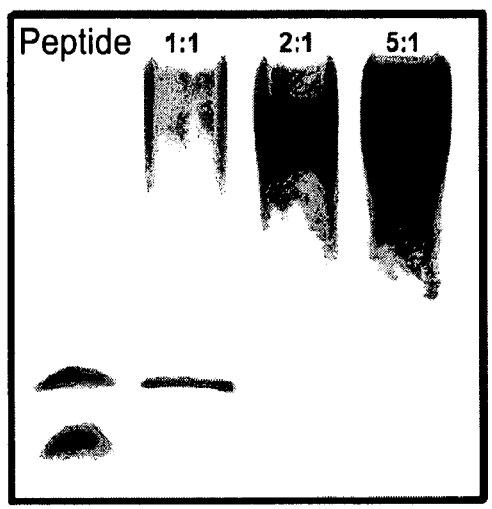
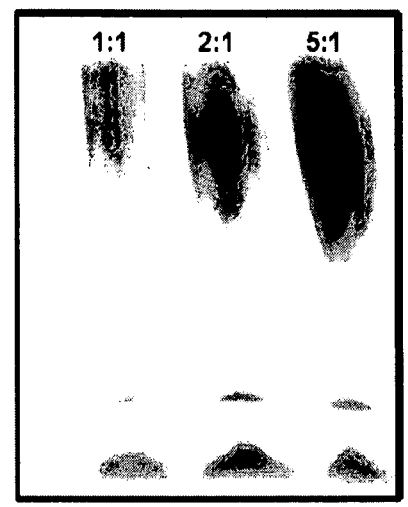
FIG. 4A  FIG. 4B
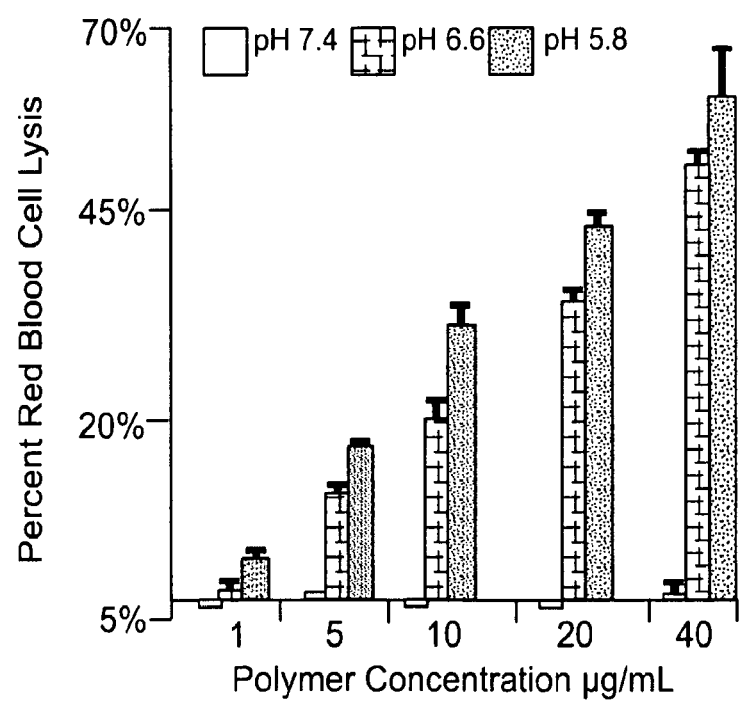
FIG. 5

PEPTIDE

CONJUGATE

SEQUENCE LISTING

```
<160> NUMBER OF SEQ ID NOS: 2

<210> SEQ ID NO 1
<211> LENGTH: 11
<212> TYPE: PRT
<213> ORGANISM: Human immunodeficiency virus type 1

<400> SEQUENCE: 1

Tyr Gly Arg Lys Lys Arg Arg Gln Arg Arg Arg
1               5                   10

<210> SEQ ID NO 2
<211> LENGTH: 38
<212> TYPE: PRT
<213> ORGANISM: Artificial Sequence
<220> FEATURE:
<223> OTHER INFORMATION: Synthetic

<400> SEQUENCE: 2

Arg Gln Ile Lys Ile Trp Phe Gln Asn Arg Arg Met Lys Trp Lys Lys
1               5                   10                  15

Met Gly Gln Val Gly Arg Gln Leu Ala Ile Ile Gly Asp Asp Ile Asn
            20                  25                  30

Arg Arg Tyr Asp Ser Cys
            35
```

BISPECIFIC INTRACELLULAR DELIVERY VEHICLES

This application is the National Stage of International Application No. PCT/US2009/043852, filed May 13, 2009, which claims the benefit of Provisional Application Nos. 61/171,381, filed Apr. 21, 2009, 61/140,779, filed Dec. 24, 2008, 61/140,774, filed Dec. 24, 2008, 61/112,054, filed Nov. 6, 2008, and 61/112,048, filed Nov. 6, 2008. Each application is incorporated herein by reference in its entirety.

STATEMENT OF JOINT RESEARCH AGREEMENT

The subject matter of the claimed invention was made as a result of activities undertaken within the scope of a joint research agreement, within the meaning of 35 U.S.C. §103(c)(3) and 37 C.F.R. §1.104(c)(4)(ii), by or on behalf of the University of Washington and PhaseRx, Inc., that was in effect on or before the claimed invention was made.

STATEMENT REGARDING FEDERALLY FUNDED RESEARCH

The invention was made with Government support under Contract No. 2R01EB002991-05A1, awarded by the National Institutes of Health. The Government has certain rights in the invention.

BACKGROUND OF THE INVENTION

The present invention is in the field of the intracellular delivery of therapeutic agents, and more particularly in the area of enhancement of transport or delivery of molecules into the cell cytosol, using bispecific affinity reagents and pH-responsive, membrane destabilizing polymers.

It is often difficult to deliver compounds, such as proteins, genetic material, and other drugs and diagnostic compounds, intracellularly because cell membranes resist the passage of these compounds. Various methods have been developed to administer agents intracellularly. For example, genetic material has been administered into cells in vivo, in vitro and ex vivo using viral vectors, DNA/lipid complexes and liposomes. DNA has also been delivered by synthetic cationic polymers and copolymers and natural cationic carriers such as chitosan. Sometimes the synthetic polymers are hydrophobically modified to enhance endocytosis. While viral vectors are efficient, questions remain regarding the safety of a live vector and the development of an immune response following repeated administration. Lipid complexes and liposomes appear less effective at transfecting DNA into the nucleus of the cell and may potentially be destroyed by macrophages in vivo.

Receptor mediated endocytosis offers an alternative means to target specific cell types and to deliver therapeutic agents intracellularly. Receptor-mediated endocytosis (RME) occurs when ligands bind to cell surface receptors on eukaryotic cell membranes, initiating or accompanying a cascade of phenomena culminating in the cellular invagination of membrane complexes within clathrin-coated vesicles. Compounds which interact with specific cell surface receptors are employed to target specific cell surface receptors. The compounds are endocytosed into the endosomes once the compounds interact with the cell surface receptors. Linkages have been made directly with the compounds, or, in the case of DNA, through conjugation with polycationic polymers such as polylysine and DEAE-dextran which are then complexed with the DNA. (Haensler et al., Bioconj. Chem., 4:372-379 (1993)).

Even after therapeutic agents are delivered intracellularly, normal trafficking in the cell can minimize their effectiveness. For example, certain antibody-antigen conjugates are readily endocytosed. However, after endocytosis, the antibody is not released into the cytosol but rather remains isolated in endosomes until it is trafficked to a lysosome for degradation. (Press, O. W. et al., Cancer Research, 48: 2249-2257 (1988)). Endosomes are membrane bound phospholipid vesicles which function in intracellular trafficking and degradation of internalized proteins. The internal pH of the endosomes is between 5.0 and 5.5. Genetic material, being negatively charged, is often complexed with polycationic materials, such as chitosan and polylysine, for delivery to a cell. Both immunotherapy and gene therapy using polycation/nucleic acid complexes are limited by trafficking of the complexes by the cell from endosomes to lysosomes, where the antibody conjugates or nucleic acids are degraded and rendered ineffective.

Protein transduction domains (PTDs) have attracted considerable interest in the drug delivery field for their ability to translocate across biological membranes. The PTDs are relatively short (11-35 amino acid) sequences that confer this apparent translocation activity to proteins and other macromolecular cargo to which they are conjugated, complexed or fused (Derossi et al., 1994; Fawell et al., 1994; Elliott and O'Hare, 1997; Schwarze et al., 2000; Snyder and Dowdy, 2001; Bennett et al., 2002).

The highly cationic 11 amino acid residue (YGRKKRRQRRR) PTD from the human immunodeficiency virus (HIV-1) TAT protein (Frankel and Pabo, 1988; Green and Loewenstein, 1988) has been one of the most well-studied translocating peptides. In-frame fusion proteins containing the TAT sequence were shown to direct cellular uptake of proteins that retained their activity intracellularly (Nagahara et al., 1998; Kwon et al., 2000; Becker-Hapak et al., 2001; Jo et al., 2001; Xia et al., 2001; Cao et al., 2002; Joshi et al., 2002; Kabouridis et al., 2002; Peitz et al., 2002). Subsequently, a diverse collection of over 60 full-length proteins with functional domains from 15 to 120 kDa have been engineered to date. Various studies employing TAT-fusion methodologies have demonstrated transduction in a variety of both primary and transformed mammalian and human cell types, including peripheral blood lymphocytes, diploid fibroblasts, keratinocytes, bone marrow stem cells, osteoclasts, HeLa cells and Jurkat T-cells (Fawell et al., 1994; Nagahara et al., 1998; Gius et al., 1999; Vocero-Akbani et al., 1999, 2000, 2001; Becker-Hapak et al., 2001). Furthermore, in vivo intracellular delivery by injection of a TAT-b-gal fusion has been demonstrated (Schwarze et al., 1999; Barka et al., 2000). However, intracellular delivery by TAT and other peptide domains is inefficient, irreproducible and in many cases results have been misleading due to artifacts caused by fixation procedures (Richard et al., *J. Biol. Chem.* 278:585, 2003).

In addition to drug delivery, there are many potential in vitro applications in areas such as drug discovery and laboratory assays that could benefit from improved intracellular delivery of biomolecules and macromolecular cargo. However, certain challenges remain. For example, even if the biomolecules and macromolecular cargo can be targeted to the desired cells and endocytosed by the cells, often are not effectively released from endosomes into the cytosol, but are degraded by lysosomes. These and other challenges are addressed by embodiments of the present invention.

SUMMARY OF THE INVENTION

Certain embodiments of the invention include a composition for delivering an agent to a cell, comprising a bispecific affinity reagent and a pH-responsive, membrane destabilizing polymer. In some embodiments, the bispecific affinity reagent comprises a single protein. In some embodiments, the bispecific affinity reagent comprises an antibody, antibody fragment, or antibody-like molecule. In some embodiments, the bispecific affinity reagent comprises a first affinity reagent covalently linked to a second affinity reagent, wherein the first affinity reagent binds to a molecule on the surface of a cell, and the second affinity reagent binds to an intracellular target. In some embodiments, the first affinity reagent and the second affinity reagent are included in a single polypeptide chain. In some embodiments, the second affinity reagent is proteinaceous. In some embodiments, the polymer is a block copolymer, such as a diblock copolymer, a triblock copolymer or a higher-order block copolymer.

Certain embodiments of the invention include a composition for delivering a biomolecular agent such as a therapeutic agent or diagnostic agent to a cell, comprising a pH-responsive, membrane destabilizing polymer having a plurality of pendant linking groups, and a bispecific affinity reagent. In some embodiments, the bispecific affinity reagent comprises a first affinity reagent linked to the polymer and a second affinity reagent linked to the polymer, wherein the first affinity reagent binds to a molecule on the surface of a cell, and the second affinity reagent binds to an intracellular target. In some embodiments, the bispecific affinity reagent comprises a plurality of first affinity reagents, wherein the plurality of first affinity reagents is linked to the polymer via the pendant linking groups. In some embodiments, the bispecific affinity reagent comprises a plurality of second affinity reagents, wherein the plurality of second affinity reagents is linked to the polymer via the pendant linking groups.

Certain embodiments of the invention include a method of altering the activity of an intracellular target in a cell, comprising contacting a cell including an intracellular target having a detectable activity with a composition comprising a pH-responsive, membrane destabilizing copolymer, and a first affinity reagent covalently linked to a second affinity reagent. In some embodiments, the first affinity reagent binds to a molecule on the surface of the cell thereby bringing the second affinity reagent into proximity with the cell surface, whereby endocytosis of at least the second affinity reagent is facilitated. In some embodiments, the pH-responsive, membrane destabilizing polymer becomes membrane-active at acidic pH, thereby causing release of at least the second affinity reagent from the endosomal compartment of the cell. In some embodiments, the second affinity reagent binds to the intracellular target after release into the interior of the cell, whereby binding of the second affinity reagent to the intracellular target detectably agonizes or antagonizes an activity of the intracellular target.

DESCRIPTION OF THE DRAWINGS

FIGS. 4A and 4B depict the results of the use of electrophoresis gels to analyze the linking of a bispecific affinity reagent to a pH-responsive membrane destabilizing polymer according to an embodiment of the present invention.

FIG. 5 is a chart depicting the results of an assay measuring the pH-dependent membrane disruption capacity of a polymer made according to an embodiment of the present invention.

DESCRIPTION OF THE INVENTION

Figure 1:
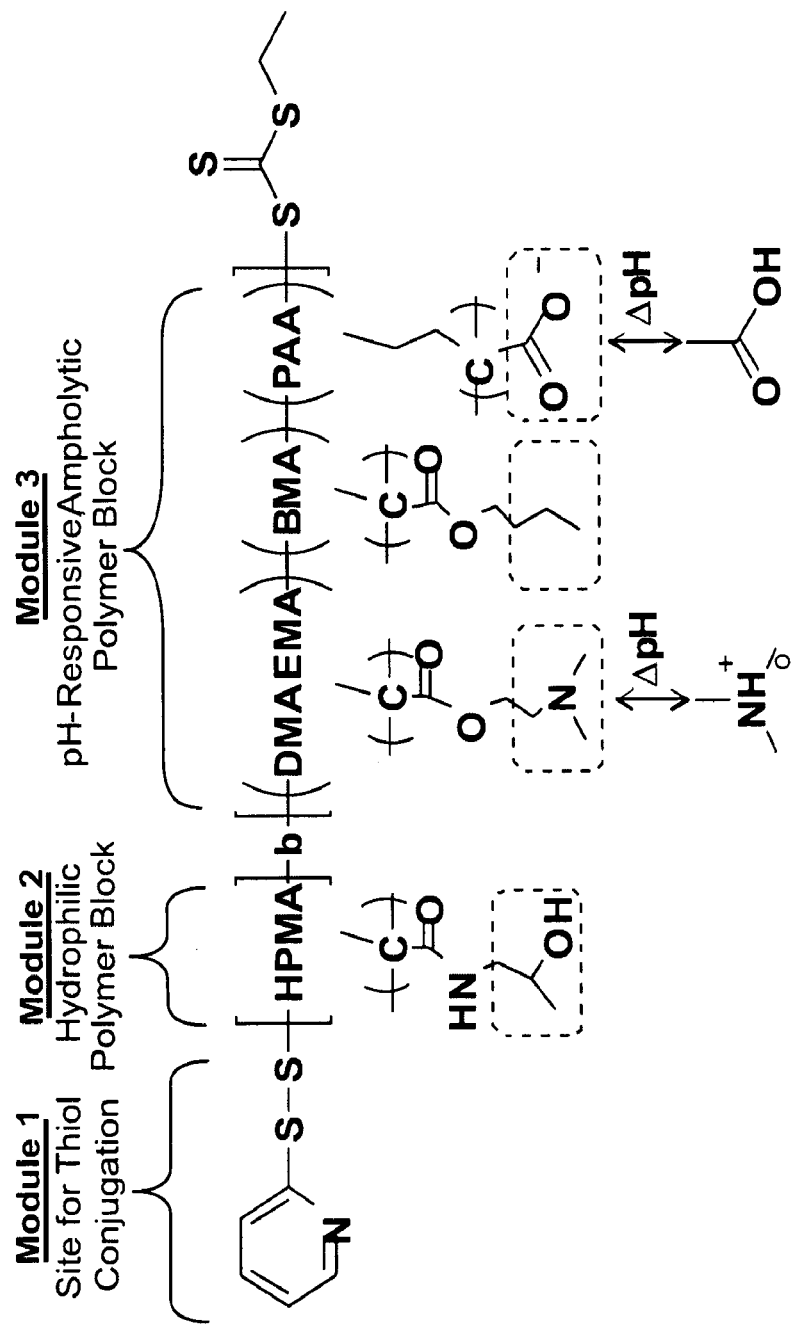
FIG. 1 is a schematic and chemical structure for a pH-responsive membrane destabilizing polymer according to an embodiment of the present invention.

The description, figures, and examples herein relate to intracellular delivery of bispecific affinity reagents using polymeric delivery vehicles Short summaries of certain terms are presented in the description of the invention. Each term is further explained throughout the description, figures, and examples. Any interpretation of the terms in this description should take into account the full description, figures, and examples presented herein. All publications recited herein are hereby incorporated by reference.

An affinity reagent is a molecule that binds to an antigen or receptor or other molecule. In some embodiments, an affinity reagent is a molecule that specifically binds to an antigen or receptor or other molecule. In certain embodiments, some or all of an affinity reagent is composed of amino acids (including natural, non-natural, and modified amino acids), nucleic acids, or saccharides. In certain embodiments, an affinity reagent is a small molecule.

Affinity reagents in certain embodiments of the present invention specifically bind to molecules or targets. A first affinity reagent binds to a cell surface antigen, a cell surface receptor, or other cell surface molecule. A second affinity reagent binds to and influences an intracellular target. A second affinity reagent is a proteinaceous affinity reagent, an aptamer, or a small molecule therapeutic of greater than 500 molecular weight. A bispecific affinity reagent comprises a first affinity reagent covalently linked to a second affinity reagent. A proteinaceous affinity reagent is an affinity reagent composed of amino acids (including natural, non-natural, and modified amino acids).

In some embodiments of the present invention, the first and second affinity reagents are proteinaceous and may be present in a single peptide or polypeptide chain. In some embodiments, the polypeptide chain is a bispecific antibody.

Bispecific antibodies are well-established in the art as a standard technique to create a single polypeptide that binds to two different determinants (Kufer et al., 2004). Bispecific antibodies may be made in many different formats, including but not limited to quadroma, F(ab')2, tetravalent, heterodimeric scFv, bispecific scFv, tandem scFv, diabody and minibody formats, or scFvs appended to or recombinantly fused with whole antibodies. (Kufer et al, 2004; Holliger and Hudson 2005; Morrison and Coloma, PCTUS94/11411).

Antibodies for use in the present invention may be raised through any conventional method, such as through injection of immunogen into mice and subsequent fusions of lymphocytes to create hybridomas. Such hybridomas may then be used either (a) to produce antibody directly, which is purified and used for chemical conjugation to create a bispecific antibody, or (b) to clone cDNAs encoding antibody fragments for subsequent genetic manipulation. To illustrate one method employing the latter strategy, mRNA is isolated from the hybridoma cells, reverse-transcribed into cDNA using antisense oligo-dT or immunoglobulin gene-specific primers, and cloned into a plasmid vector. Clones are sequenced and characterized. They may then be engineered according to standard protocols to combine the heavy and light chains of each antibody, separated by a short peptide linker, into a bacterial or mammalian expression vector as previously described to produce a recombinant bispecific antibody, which are then expressed and purified according to well-established protocols in bacteria or mammalian cells (Kufer et al, 2004; Antibody Engineering: A Practical Approach, McCafferty, Hoogenboom and Chiswell Eds, IRL Press 1996). Antibodies, or other proteinaceous affinity molecules such as peptides, may also be created through display technologies that allow selection of interacting affinity reagents through the screening of very large libraries of, for example, immunoglobulin domains or peptides expressed by bacteriophage (Antibody Engineering: A Practical Approach, McCafferty, Hoogenboom and Chiswell Eds, IRL Press 1996). Antibodies of the present invention may also be humanized through grafting of human immunoglobulin domains, or made from transgenic mice or bacteriophage libraries that have human immunoglobulin genes/cDNAs.

In some embodiments of the invention, first and second affinity reagents may comprise proteinaceous structures other than antibodies that are able to bind to protein targets specifically, including but not limited to avimers (Silverman et al, 2005), ankyrin repeats (Zahnd et al., 2007) and adnectins (as described in U.S. Pat. No. 7,115,396), and other such proteins with domains that can be evolved to generate specific affinity for antigens, collectively referred to as "antibody-like molecules". Modifications of proteinaceous affinity reagents through the incorporation of unnatural amino acids during synthesis may be used to improve their properties (see Datta et al., 2002; and Liu et al., 2007). Such modifications may have several benefits, including the addition of chemical groups that facilitate subsequent conjugation reactions.

In some embodiments, the first or second affinity reagent may be a peptide. In some embodiments, the peptide chain is a bispecific peptide. Peptides can readily be made and screened to create affinity reagents that recognize and bind to macromolecules such as proteins (see, for example, "Phage display of combinatorial peptide and protein libraries and their applications in biology and chemistry". Current Topics in Microbiology and Immunology, vol. 243 1999, p. 87-105).

In some embodiments of the invention, proteinaceous first and proteinaceous second affinity reagents are present on two separate peptide or polypeptide chains. Bispecific affinity reagents may be constructed by separate synthesis and expression of the first and second affinity reagents. A polypeptide bispecific reagent can be expressed as two separately encoded chains that are linked by disulfide bonds during production in the same host cell, such as, for example, a bispecific scFv or diabody (Kufer et al., 2004; Holliger and Hudson, 2005). Similarly, standard and widely used solid-phase peptide synthesis technology (see, for example, Handbook of Reagents for Organic Synthesis, Reagents for Glycoside, Nucleotide, and Peptide Synthesis, David Crich (Ed.) 2005) can be used to synthesize peptides, and chimeric bispecific peptides are well known in the art (see, for example, Dickey et al., *J Biol Chem* 283:35003, 2008). A bispecific peptide strategy may be used to combine the first and second first and second affinity reagents in a single peptide chain. Alternatively, polypeptide chains or peptide chains can be expressed/synthesized separately, purified and then conjugated chemically to produce the bispecific affinity reagents of the present invention. Many different formats of antibodies may be used. Whole antibodies, F(ab')2, F(ab'), scFv, as well as smaller Fab and single-domain antibody fragments (Holliger and Hudson, 2005) may all be used to create the first and second affinity reagents. Following their expression and purification, the first and second affinity reagents can be chemically conjugated to create the bispecific affinity reagent. Many conjugation chemistries may be used to effect this conjugation, including homofunctional or heterofunctional linkers that yield ester, amide, thioether, carbon-carbon, or disulfide linkages (see *Bioconjugation*, Aslam and Dent, Eds, Macmillan, 1998 and chapters therein). The first and second affinity reagents may also be linked to each other via the polymer itself (see below).

In some embodiments, first affinity reagents are peptide aptamers. A peptide aptamer is a peptide molecule that specifically binds to a target protein, and interferes with the functional ability of that target protein (Kolonin et al., *Proc. Natl. Acad. Sci. USA* 95:14266 (1998). Peptide aptamers consist of a variable peptide loop attached at both ends of a protein scaffold. Such peptide aptamers can often have a binding affinity comparable to that of an antibody (nanomolar range). Due to the highly selective nature of peptide aptamers, they can be used not only to target a specific protein, but also to target specific functions of a given protein (e.g., a signaling function).

Peptide aptamers are usually prepared by selecting the aptamer for its binding affinity with the specific target from a random pool or library of peptides. Peptide aptamers can be isolated from random peptide libraries by yeast two-hybrid screens (Xu et al., *Proc. Natl. Acad. Sci. USA* 94:12473 (1997). They can also be isolated from phage libraries (Hoogenboom et al., Immunotechnology 4:1 (1998) or chemically generated peptides/libraries.

First affinity reagents may also be nucleic acid aptamers. Nucleic acid aptamers are nucleic acid oligomers that bind other macromolecules specifically; such aptamers that bind specifically to other macromolecules can be readily isolated from libraries of such oligomers by technologies such as SELEX (see, for example, "SELEX—a (r)evolutionary method to generate high-affinity nucleic acid ligands", Stoltenburg et al., *Biomol. Eng.* 24:381, 2007).

In some embodiments, first affinity reagents are oligosaccharides. Certain oligosaccharides are known ligands for certain extracellular or cell surface receptors. For example, Collins et al. describe a synthetic sialoside with affinity for cellular protein CD22. ("High-Affinity Ligand Probes of CD22 Overcome the Threshold Set by cis Ligands to Allow for Binding, Endocytosis, and Killing of B Cells" Collins et al., *J. Immunol.* 177:2994-3003, 2006).

The first affinity reagent recognizes a cell surface antigen on the target cell. The first affinity reagent may be an antibody, antibody-like molecule, or a peptide, such as an integrin-binding RGD peptide, or a small molecule, such as vitamins, e.g., folate, sugars such as lactose and galactose, or other small molecules. The cell surface antigen may be any cell surface molecule that undergoes internalization, such as a protein, sugar, lipid head group or other antigen on the cell surface. Examples of cell surface antigens useful in the context of the present invention include but are not limited to the transferrin receptor type 1 and 2, the EGF receptor, HER2/

Neu, VEGF receptors, integrins, CD33, CD19, CD20, CD22 and the asialoglycoprotein receptor.

First affinity reagents may also include peptide transduction domains such as the VP22 uptake peptide from HSV, the HIV TAT protein/peptide, and the antennapedia peptide, the transportan peptide, and polyarginine. Peptide transduction domains are known in the art, as described, for example, in Snyder EL, Dowdy SF. Recent advances in the use of protein transduction domains for the delivery of peptides, proteins and nucleic acids in vivo. Expert Opin. Drug Deliv. 2005 January; 2(1):43-51.

In some embodiments, second affinity reagents are the antibodies, antibody-like molecules, peptides, aptamers, or small molecules. In some embodiments, second affinity reagents are dominant negative proteins. Certain dominant negative proteins have been shown to inhibit VEGF promoter activity. (*J Biol Chem* 274(44):31565-31570, Oct. 29, 1999)

The second affinity reagent recognizes an intracellular target. This "effector" affinity reagent binds specifically to an intracellular antigen, such as a protein. In some embodiments, the second affinity reagent is proteinaceous, and in certain embodiments is an antibody or antibody-like molecule. Other second affinity reagents include peptides, such as for example the bcl-2 antagonist BH3 peptide (Walsh et al., 2002), and organic macromolecules which by virtue of their size (a molecular weight of >500 g), charge, or other physicochemical properties, are unable or poorly able to enter cells. In some embodiments, the second affinity reagent is a nucleic acid aptamer. The second affinity reagent may bind to cytosolic proteins; proteins bound to the inner face of the plasma membrane, or the nuclear, mitochondrial or other membranes in the cell; or nuclear proteins or proteins in other subcellular compartments. It will be evident to those skilled in the art that affinity reagents which block critical functions of intracellular signaling will be good candidates for use as second affinity reagents. Second affinity reagents may directly inhibit the activity of a protein, or block an interaction with a protein's substrate, or they may block protein-protein interactions. Also, it is well established that some affinity reagents are able to rescue defects in intracellular proteins. Such second affinity reagents may therefore act as agonists of the activity of an intracellular protein. This has been clearly shown in the case of antibodies against the p53 protein, in which antibodies can increase the DNA binding and transcriptional activity of the p53 mutants found in many cancer cells, which would enable correction of this mutation in the p53 tumor suppressor in cancer cells (see Abarzua et al., *Cancer Res.* 55(16):3490-4, Aug. 15, 1995). Specific protein families that may be targeted by the second affinity reagent include kinases, such as the receptor tyrosine kinases including the intracellular domains of the EGF, HER2/neu, PDGF, and VEGF receptors, ion channel receptors, G protein receptors and the intracellular domains of other cell surface receptors; cellular kinases such as erk, mek, map kinase (mapK), mapKK, mapKKK, and their substrates such as mitogen-activated protein kinase activated protein kinases (MAPKAPKs), including MAPKAPK2; GTPases such as the h-, k-, and n-ras proteins; phosphatases; proteins involved in apoptosis pathways such as the bcl-2 proteins and associated family members; transcription factors; and all other intracellular proteins. In certain embodiments, the proteinaceous second affinity reagent is a naturally occurring cellular protein. In some embodiments, second affinity reagents that are proteins may include those used to correct a genetic deficiency by exogenously providing the missing protein in association with the polymer vehicles of the present invention (such as, for example, glucocerebrosidase deficiency to correct symptoms of Gauchers Disease); proteins used to supplement/add protein function to a cell; dominant-negative proteins; enzymes; and other proteins of therapeutic value.

The first and second affinity reagents may be directly covalently linked to each other through a covalent bond. Alternatively, the first and second affinity reagents are linked to each other through a linker. The linker may be a peptide linker or a chemical linker. Specific embodiments contemplate a linker that is a glycine succinate linker, an amino acid linker or combination thereof. Other linkers include, but are not limited to, a disulfide linker, carbonate linker; imine linker resulting from reaction of an amine and an aldehyde; phosphate ester linkers formed by reacting an alcohol with a phosphate group; hydrazone linkers which are reaction product of a hydrazide and an aldehyde; acetal linkers that are the reaction product of an aldehyde and an alcohol; orthoester linkers that are the reaction product of a formate and an alcohol; peptide linkages formed by an amine group, including but not limited to, at an end of a polymer such as PEG, and a carboxyl group of a peptide. As described herein, linking does not include ionic or other non-covalent bonding, such as via a biotin-streptavidin linkage.

Bispecific proteinaceous affinity reagents, or component proteinaceous affinity reagents, may be expressed in bacterial, fungal or mammalian expression systems and purified by standard chromatographic techniques (Antibody Engineering: A Practical Approach, McCafferty, Hoogenboom and Chiswell Eds, IRL Press 1996).

Following their expression/synthesis and purification, the first and second affinity reagents are associated with the pH-responsive, membrane destabilizing polymer through a covalent coupling. If the first and second affinity reagents are present as one chemical entity, either through recombinant fusion, or chemical conjugation or association, the bispecific affinity reagent is covalently associated with the polymer. Alternatively, the first and second affinity reagents may be separately expressed and separately covalently associated with the polymer to create the bispecific affinity reagent.

A pH-responsive, membrane destabilizing polymer is a polymer that at about physiologic pH (7.4) undergoes a transition at the lower pH environment of the endosome and becomes membrane destabilizing. In some non-limiting embodiments of the invention the polymers can be made of homopolymers of alkyl acrylic acids, such as butyl acrylic acid (BAA) or propyl acrylic acid (PAA), or can be copolymers of ethyl acrylic acid (EAA) (Jones et al, 2003, Murthy et al., 2003). Polymers of alkyl amine or alkyl alcohol derivatives of maleic-anhydride copolymers with methyl vinyl ether or styrene may also be used. In some embodiments, the polymers can be made as copolymers with other monomers. The addition of other monomers can enhance the potency of the polymers, or add chemical groups with useful functionalities to facilitate association with other molecular entities, including the bispecific affinity reagent and/or other adjuvant materials such as poly(ethylene glycol). These copolymers may include, but are not limited to, copolymers with monomers containing groups that can be crosslinked to the bispecific affinity reagent. In an exemplary embodiment, a copolymer of poly(propylacrylic acid) (PAA)-co-pyridyl disulfide acrylate (PDSA), p(PAA-co-PDSA) (El-Sayed et al., 2005) is conjugated via disulfide exchange between the PDSA component of the polymer and free thiols introduced into the proteinaceous affinity reagent by reaction with Traut's reagent (2-iminothiolane, Pierce Biotechnology, Rockford, Ill.). Similar strategies using monomers comprising other functionalities to enable conjugation, such as NHS, azide and alkyne monomers, may also be used.

The polymer can also serve as the vehicle through which the first and second affinity reagents are linked, in addition to providing its functional properties of pH-responsive membrane destabilization. Conjugation of the first and second affinity reagents to the polymers may be achieved by using polymers with telechelic ends. These different ends allow separate conjugation of the first and second affinity reagents. In this way, a bispecific affinity reagent is made by linking the first and second affinity reagent to either end of the same polymer molecule.

The first and/or second affinity reagent may also be linked to the polymer via pendant linking groups of the polymer chain. Pendant groups that may be used for such conjugation include carboxyl residues such as those present on the alkyl acrylic acids, as well as chemical groups on other monomers introduced via copolymerization, such as PDSA.

Generally, the various polymers included as constituent moieties of the compounds of the invention can comprise one or more repeat units—monomer (or monomeric) residues—derived from a process which includes polymerization. Such monomeric residues can optionally also include structural moieties (or species) derived from post-polymerization (e.g., derivatization) reactions. Monomeric residues are constituent moieties of the polymers, and accordingly, can be considered as constitutional units of the polymers. Generally, a polymer of the invention can comprise constitutional units which are derived (directly or indirectly via additional processes) from one or more polymerizable monomers.

Generally, each polymer can be a homopolymer (derived from polymerization of one single type of monomer—having essentially the same chemical composition) or a copolymer (derived from polymerization of two or more different monomers—having different chemical compositions). Polymers which are copolymers include random copolymer chains or block copolymer chains (e.g., diblock copolymer, triblock copolymer, higher-ordered block copolymer, etc). Any given block copolymer chain can be conventionally configured and effected according to methods known in the art.

Generally, each polymer can be a linear polymer, or a non-linear polymer. Non-linear polymers can have various architectures, including for example branched polymers, brush polymers, star-polymers, dendrimer polymers, and can be cross-linked polymers, semi-cross-linked polymers, graft polymers, and combinations thereof.

Polymers of the present invention may be carried out by methods including Atom Transfer Radical Polymerization (ATRP), nitroxide-mediated living free radical polymerization (NMP), ring-opening polymerization (ROP), degenerative transfer (DT), or Reversible Addition Fragmentation Transfer (RAFT). In specific embodiments, a polymer can be a prepared by controlled (living) radical polymerization, such as reversible addition-fragmentation chain transfer (RAFT) polymerization. Such methods and approaches are generally known in the art, and are further described herein. Alternatively, a polymer can be a prepared by conventional polymerization approaches, including conventional radical polymerization approaches.

Generally, a polymer is prepared by a method other than by stepwise coupling approaches involving a sequence of multiple individual reactions (e.g., such as known in the art for peptide synthesis or for oligonucleotide synthesis). The backbone of the membrane-destabilizing polymer is not a peptidic polymer, a nucleic acid polymer, or a lipid polymer. In contrast, for clarity, notwithstanding and without prejudice to the foregoing, the affinity reagents and/or other biomolecular agents of the inventions can be an amino acid polymer (e.g., a peptide) or a nucleic acid polymer (e.g., an oligonucleotide).

Generally, polymers prepared by controlled (living) radical polymerization, such as reversible addition-fragmentation chain transfer (RAFT) polymerization, may include moieties other than the monomeric residues (repeat units). For example, and without limitation, such polymers may include polymerization-process-dependent moieties at the α-end or at the ω-end of the polymer chain. Typically, for example, a polymer chain derived from controlled radical polymerization such as RAFT polymerization may further comprise a radical source residue covalently coupled with the α-end thereof. For example, the radical source residue can be an initiator residue, or the radical source residue can be a leaving group of a reversible addition-fragmentation chain transfer (RAFT) agent. Typically, as another example, a polymer derived from controlled radical polymerization such as RAFT polymerization may further comprise a chain transfer residue covalently coupled with the ω-end thereof. For example, a chain transfer residue can be a thiocarbonylthio moiety having a formula —SC(=S)Z, where Z is an activating group. Typical RAFT chain transfer residues are derived from radical polymerization in the presence of a chain transfer agent selected from xanthates, dithiocarbamates, dithioesters, and trithiocarbonates. The process-related moieties at α-end or at the ω-end of the polymer or between blocks of different polymers can comprise or can be derivatized to comprise functional groups, e.g., suitable for covalent linking, etc.

Further aspects of the polymers are disclosed in the following paragraphs, including preferred polymerizable monomers from which the repeat units of the polymers are derived.

In preferred embodiments, the polymers can comprise repeat units derived from ethylenically unsaturated monomers. The term "ethylenically unsaturated monomer" is defined herein as a compound having at least one carbon double or triple bond. The non-limiting examples of the ethylenically unsaturated monomers are: an alkyl (alkyl)acrylate, a alkyl methacrylate, an alkylacrylic acid, an N-alkylacrylamide, a methacrylamide, a styrene, an allylamine, an allylammonium, a diallylamine, a diallylammonium, an n-vinyl formamide, a vinyl ether, a vinyl sulfonate, an acrylic acid, a sulfobetaine, a carboxybetaine, a phosphobetaine, or maleic anhydride.

In various embodiments, any monomer suitable for providing the polymers described herein may be used to effect the invention. In some embodiments, monomers suitable for use in the preparation of polymers provided herein include, by way of non-limiting example, one or more of the following monomers: methyl methacrylate, ethyl acrylate, propyl methacrylate (all isomers), butyl methacrylate (all isomers), 2-ethylhexyl methacrylate, isobornyl methacrylate, methacrylic acid, benzyl methacrylate, phenyl methacrylate, methacrylonitrile, alpha-methylstyrene, methyl acrylate, ethyl acrylate, propyl acrylate (all isomers), butyl acrylate (all isomers), 2-ethylhexyl acrylate, isobornyl acrylate, acrylic acid, benzyl acrylate, phenyl acrylate, acrylonitrile, styrene, acrylates and styrenes selected from glycidyl methacrylate, 2-hydroxyethyl methacrylate, hydroxypropyl methacrylate (all isomers), hydroxybutyl methacrylate (all isomers), N,N-dimethylaminoethyl methacrylate, N,N-diethylaminoethyl methacrylate, triethyleneglycol methacrylate, itaconic anhydride, itaconic acid, glycidyl acrylate, 2-hydroxyethyl acrylate, hydroxypropyl acrylate (all isomers), hydroxybutyl acrylate (all isomers), N,N-dimethylaminoethyl acrylate, N,N-diethylaminoethyl acrylate, triethyleneglycol acrylate, methacrylamide, N-methylacrylamide, N,N-di methylacrylamide, N-tert-butylmethacrylamide, N-n-butylmethacrylamide, N-methylolacrylamide, N-ethylolacrylamide, vinyl benzoic acid (all isomers), diethylaminostyrene (all isomers), alpha-methylvinyl benzoic acid (all isomers), diethylamino alpha-methylstyrene (all isomers), p-vinylbenzenesulfonic acid, p-vinylbenzene sulfonic sodium salt, trimethoxysilylpropyl methacrylate, triethoxysilylpropyl methacrylate, tributoxysilylpropyl methacrylate, di methoxymethylsilylpropyl methacrylate, diethoxymethylsilylpropylmethacrylate, dibutoxymethylsilylpropyl methacrylate, diisopropoxymethylsilylpropyl methacrylate, dimethoxysilylpropyl methacrylate, diethoxysilylpropyl methacrylate, dibutoxysilylpropyl methacrylate, diisopropoxysillpropyl methacrylate, trimethoxysilylpropyl acrylate, triethoxysilylpropyl acrylate, tributoxysilylpropyl acrylate, dimethoxymethylsilylpropyl acrylate, diethoxymethylsilylpropyl acrylate, dibutoxymethylsilylpropyl acrylate, diisopropoxymethylsilylpropyl acrylate, dimethoxysilylpropyl acrylate, diethoxysilylpropyl acrylate, dibutoxysilylpropyl acrylate, diisopropoxysilylpropyl acrylate, vinyl acetate, vinyl butyrate, vinyl benzoate, vinyl chloride, vinyl fluoride, vinyl bromide, maleic anhydride, N-arylmaleimide, N-phenylmaleimide, N-alkylmaleimide, N-butylimaleimide, N-vinylpyrrolidone, N-vinylcarbazole, butadiene, isoprene, chloroprene, ethylene, propylene, 1,5-hexadienes, 1,4-hexadienes, 1,3-butadienes, 1,4-pentadienes, vinylalcohol, vinylamine, N-alkylvinylamine, allylamine, N-alkylallylamine, diallylamine, N-alkyldiallylamine, alkylenimine, acrylic acids, alkylacrylates, acrylamides, methacrylic acids, alkylmethacrylates, methacrylamides, N-alkylacrylamides, N-alkylmethacrylamides, styrene, vinylnaphthalene, vinyl pyridine, ethylvinylbenzene, aminostyrene, vinylimidazole, vinylpyridine, vinylbiphenyl, vinylanisole, vinylimidazolyl, vinylpyridinyl, vinylpolyethyleneglycol, dimethylaminomethylstyrene, trimethylammonium ethyl methacrylate, trimethylammonium ethyl acrylate, dimethylamino propylacrylamide, trimethylammonium ethylacrylate, trimethylanunonium ethyl methacrylate, trimethylammonium propyl acrylamide, dodecyl acrylate, octadecyl acrylate, or octadecyl methacrylate monomers, or combinations thereof.

In some embodiments, polymers can be derived from certain specific monomers and combinations of monomers, for example, for use in connection with various embodiments, such as for uses associated with proteinaceous compositions. Such preferred polymers are described below.

Generally, polymers can include repeat units derived from functionalized monomers, including versions of the aforementioned monomers. A functionalized monomer, as used herein, can include a monomer comprising a masked (protected) or non-masked (unprotected) functional group, e.g., a group to which other moieties, can be covalently attached following the polymerization. The non-limiting examples of such groups are primary amino groups, carboxyls, thiols, hydroxyls, azides, and cyano groups. Several suitable masking groups are available (see, e.g., T. W. Greene & P. G. M. Wuts, Protective Groups in Organic Synthesis (2nd edition) J. Wiley & Sons, 1991. P. J. Kocienski, Protecting Groups, Georg Thieme Verlag, 1994).

As used herein, a "block" copolymer refers to a structure comprising one or more sub-combination of constitutional or monomeric units. In some embodiments, the block copolymer is a diblock copolymer, a tri-block copolymer or a higher-ordered block copolymer. For example, a diblock copolymer can comprise two blocks; a schematic generalization of such a polymer is represented by the following: [Aa/Bb/Cc/ . . . ]m-[Xx/Yy/Zz/ . . . ]n, wherein each letter stands for a constitutional or monomeric unit, and wherein each subscript to a constitutional unit represents the mole fraction of that unit in the particular block, the three dots indicate that there may be more (there may also be fewer) constitutional units in each block and m and n indicate the molecular weight (or weight fraction) of each block in the diblock copolymer. As suggested by such schematic representation, in some instances, the number and the nature of each constitutional unit is separately controlled for each block. The schematic is not meant to, and should not be construed to, infer any relationship whatsoever between the number of constitutional units or between the number of different types of constitutional units in each of the blocks. Nor is the schematic meant to describe any particular number or arrangement of the constitutional units within a particular block. In each block the constitutional units may be disposed in a purely random, an alternating random, a regular alternating, a regular block or a random block configuration unless expressly stated to be otherwise. A purely random configuration, for example, may have the form: x-x-y-z-x-y-y-z-y-z-z-z . . . An exemplary alternating random configuration may have the form: x-y-x-z-y-x-y-z-y-x-z . . . , and an exemplary regular alternating configuration may have the form: x-y-z-x-y-z-x-y-z . . . An exemplary regular block configuration may have the following general configuration: . . . x-x-x-y-y-y-z-z-z-x-x-x . . . , while an exemplary random block configuration may have the general configuration: . . . x-x-x-z-z-x-x-y-y-y-y-z-z-z-x-x-z-z-z- . . . In a gradient polymer, the content of one or more monomeric units increases or decreases in a gradient manner from the α end of the polymer to the ω end. In none of the preceding generic examples is the particular juxtaposition of individual constitutional units or blocks or the number of constitutional units in a block or the number of blocks meant nor should they be construed as in any manner bearing on or limiting the actual structure of block copolymers forming the polymeric carrier of this invention.

As used herein, the brackets enclosing the constitutional units are not meant and are not to be construed to mean that the constitutional units themselves form blocks. That is, the constitutional units within the square brackets may combine in any manner with the other constitutional units within the block, i.e., purely random, alternating random, regular alternating, regular block or random block configurations. The block copolymers described herein are, optionally, alternate, gradient or random block copolymers.

A unimer or monoblock polymer is a synthetic product of a single polymerization step. The term monoblock polymer includes a copolymer such as a random copolymer (i.e. a product of polymerization of more than one type of monomers) and a homopolymer (i.e. a product of polymerization of a single type of monomers).

Methods for preparing polymers are described below, and are generally applicable for, but not be limiting of, the polymers described herein.

Membrane Destabilizing Polymers

As used herein, "membrane-destabilizing" or "destabilizing of a cell membrane" refers to the ability of a composition comprising one or more membrane destabilizing polymers to elicit a permeability change in a cellular membrane structure (e.g., an endosomal membrane) so as to permit macromolecules or biomolecules, in combination with or independent of a polymer or micellic assembly described herein, to enter a cell or to exit a cellular vesicle (e.g., an endosome). This permeability change can be functionally defined by the polymer's activity in assays that, for example, measure red blood cell lysis (hemolysis) or by release of nucleic acid or peptide molecules from cellular endosomal compartments. Complete membrane disruption refers to a mechanism thought to result in the lysis of the endosome.

In certain embodiments, the polymer can be or comprise at least one or more polymers (including for example as regions or segments, such as a block of a block copolymer) which comprise a membrane destabilizing polymer. In other embodiments, the polymer can be or comprise at least one membrane disruptive polymer. Preferred polymers provided herein can be a cellular membrane destabilizing polymer (e.g., is disruptive of a cellular membrane), such as, by way of non-limiting example, an extracellular membrane, an intracellular membrane, a vesicle, an organelle, an endosome, a liposome, or a red blood cell. Preferably, in certain instances, wherein a polymer described herein is in contact with a cellular membrane, it disrupts the membrane and enters the intracellular environment. In specific embodiments, a polymer provided herein is hemolytic. In specific embodiments, a polymer provided herein is endosomolytic.

The membrane destabilizing or membrane disruptive polymer can be a pH sensitive polymer having membrane destabilizing activity or membrane disrupting activity at a desired pH. In some embodiments, membrane destabilizing polymers (e.g., copolymers) or membrane destabilizing block copolymers provided herein are membrane destabilizing (e.g., in an aqueous medium) at an endosomal pH. In some embodiments, the membrane destabilizing block copolymers are membrane destabilizing (e.g., in an aqueous medium) at a pH of about 6.5 or lower, preferably at a pH ranging from about 5.0 to about 6.5, or at a pH of about 6.2 or lower, preferably at a pH ranging from about 5.0 to about 6.2, or at a pH of about 6.0 or lower, preferably at a pH ranging from about 5.0 to about 6.0.

Preferably, in each case, the membrane destabilizing polymer can have membrane destabilizing activity or membrane disrupting activity at a desired quantity (e.g., concentration) of polymer. A membrane destabilizing or membrane disruptive characteristic of a polymer can be determined by suitable assays known in the art. For example, membrane-destabilizing activity or membrane-disruptive activity of a polymer can be determined in an in vitro cell assay such as the red blood cell hemolysis assay. An endosomolytic polymer activity can be determined in an in vitro cell assay.

In general, the membrane destabilizing polymer is composed of monomeric residues with particular properties. Anionic monomeric residues comprise a species charged or chargeable to an anion, including a protonatable anionic species. Anionic monomeric residues can be anionic at an approximately neutral pH of 7.2-7.4. Cationic monomeric residues comprise a species charged or chargeable to a cation, including a deprotonatable cationic species. Cationic monomeric residues can be cationic at an approximately neutral pH of 7.2-7.4. Hydrophobic monomeric residues comprise a hydrophobic species. Hydrophilic monomeric residues comprise a hydrophilic species.

Preferably in this regard, for example, the polymer can be or comprise at least one polymer chain which is hydrophobic. Preferably in this regard, the polymer can be or comprise at least one polymer chain which includes a plurality of (anionic) monomeric residues. In this regard, for example, the polymer can preferably be or comprise at least one polymer chain which includes (i) a plurality of hydrophobic monomeric residues having a hydrophobic species, and (ii) a plurality of (anionic) monomeric residues which can preferably be anionic at approximately neutral pH, and substantially neutral or non-charged at an endosomal pH or weakly acidic pH.

In such aforementioned embodiments, the polymer can further comprise a plurality of cationic species. Accordingly, for example, the polymer can be or comprise at least one polymer chain which includes a plurality of anionic monomeric residues (e.g., having species that are anionic at about neutral pH), and a plurality of hydrophobic monomeric residues (e.g., having hydrophobic species), and optionally a plurality of cationic monomeric residues (e.g., having species that are cationic at about neutral pH). In such embodiments, and as discussed further below, the polymer can be or comprise at least one polymer chain which is charge modulated, and preferably charge balanced—being substantially overall neutral in charge.

In some embodiments the membrane destabilizing or membrane destabilizing polymer can be block copolymer, and can comprise a membrane destabilizing segment (e.g., as a block or region of the polymer). The membrane destabilizing segment can comprise a plurality of anionic monomeric residues (e.g., having species that are anionic at about neutral pH), and a plurality of hydrophobic monomeric residues (e.g., having hydrophobic species), and optionally a plurality of cationic monomeric residues (e.g., having species that are cationic at about neutral pH). In such embodiments, the segment (e.g., block or region) can be hydrophobic considered in the aggregate. In such embodiments, the block copolymer may further comprise a hydrophilic segment.

As a general, non-limiting example, a composition can comprise polymers which comprise a block copolymer, where the block copolymer comprises one or more polymer chains (e.g., with each such chain defining a polymer block), with at least polymer chain being or comprising a membrane destabilizing polymer (e.g., such as an endosomal membrane destabilizing polymer). For example, in one orientation, the block copolymer can preferably comprise a first polymer chain defining a first block A of the copolymer, and a second membrane destabilizing polymer chain defining a second block B of the copolymer. For example, the block copolymer can comprise a first polymer chain defining a first block A of the copolymer, which is hydrophilic, and a second polymer chain defining a second block B of the copolymer which includes (i) a plurality of hydrophobic monomeric residues, and (ii) a plurality of anionic monomeric residues being anionic at serum physiological pH, and being substantially neutral or non-charged at an endosomal pH.

In some embodiments of the invention, the polymer can be or comprise at least one polymer chain which includes a plurality of anionic monomeric residues, a plurality of hydrophobic monomeric residues, and optionally a plurality of cationic monomeric residues in ratios adapted to enhance membrane destabilizing or membrane destabilizing activity of the polymer chain. For example and without limitation, in such embodiments at pH 7.4, the ratio of hydrophobic: (anionic+cationic) species ranges from about 1:2 to about 3:1, and the ratio of anionic: cationic species ranges from about 1:0 to about 1:4. In other such embodiments, at pH 7.4, the ratio of hydrophobic: (anionic+cationic) species ranges from about 1:1 to about 2:1, and the ratio of anionic: cationic species ranges from about 4:1 to about 1:4.

Generally, the polymer can be or comprise at least one polymer chain which is charge modulated, for example including hydrophobic monomeric residues together with both anionic monomeric residues and cationic monomeric residues. The relative ratio of anionic monomeric residues and cationic monomeric residues can be controlled to achieve a desired overall charge characteristic. In preferred embodiments, for example, such polymer or polymer chain can be charge balanced—having a substantially neutral overall charge in an aqueous medium at physiological pH (e.g., pH 7.2 to 7.4).

Embodiments comprising a block copolymer, in which at least one block is or comprises a membrane destabilizing polymer, such as a hydrophobic membrane destabilizing polymer, can comprise one or more further polymer chains as additional blocks of the block copolymer. Generally, such further polymer blocks are not narrowly critical, and can be or comprise a polymer chain which is hydrophilic, hydrophobic, amphiphilic, and in each case, which is neutral, anionic or cationic in overall charge characteristics.

In embodiments of the invention, the polymer can be or comprise a polymer chain which is adapted to facilitate one or more additional constituent components and/or functional features of the compound or composition of the invention. For example, such polymer chain can comprise an end functional group (e.g., on the alpha end or omega end of the polymer chain) adapted for covalently linking, directly or indirectly, to an affinity reagent, or a shielding agent. Additionally or alternatively, such polymer chain can comprise one or more monomeric residues having a pendant functional group adapted for conjugating to an agent. Such conjugatable monomeric residues can be effected for covalently linking, directly or indirectly, to an affinity reagent, a shielding agent, or other biomolecular agent. Additionally or alternatively, such polymer chain can comprise one or more monomeric residues having a shielding species. For example, shielding monomeric residues can be derived directly from a polymerization reaction which includes polymerizable monomers comprising a shielding moiety. Shielding agents include poly ethylene glycol monomers and/or polymers. Additionally or alternatively, such polymer chain can comprise one or more monomeric residues having a two or more pendant functional groups—suitable for crosslinking between polymer chains. Such crosslinking monomeric residues can be a constituent moiety of a crosslinked polymer or polymer chain, as derived directly from a polymerization reaction which includes one or more polymerizable monomers comprising a multi-functional (e.g., bis-functional) crosslinking monomer. Various additional aspects and specific features of such agents and such moieties, including biomolecular agents, targeting agents, shielding agents conjugating moieties and crosslinking moieties are discussed herein.

Generally, one or more blocks of a block copolymer can be a random copolymer block which comprises two or more compositionally distinct monomeric residues.

Generally, a single monomeric residue can include multiple moieties having different functionality—e.g., can comprise hydrophobic species as well as anionic species, or e.g., can comprise hydrophobic species as well as cationic species, or e.g., can comprise anionic species as well as cationic species. Hence, in any embodiment, the polymer can be or can comprise a polymer comprising a monomeric residue such as an anionic hydrophobic monomeric residue—which includes hydrophobic species and anionic species (e.g., species which are anionic at about neutral pH).

Anionic monomeric residues can preferably comprise a protonatable anionic species. Considered in the aggregate, as incorporated into a polymer chain, such anionic monomeric residues can be substantially anionic at a pH of or greater than 7.0 and substantially neutral (non-charged) at pH of or less than 6.0. Preferably, such anionic monomeric residues can have a pKa ranging from about 5.5 to about 6.8. Anionic monomeric residues can independently comprise a plurality of monomeric residues having a protonatable anionic species selected from carboxylic acid, sulfonamide, boronic acid, sulfonic acid, sulfinic acid, sulfuric acid, phosphoric acid, phosphinic acid, and phosphorous acid groups, and combinations thereof. Preferred anionic monomeric residues can be derived from polymerization of a ($C_2$-$C_8$) alkylacrylic acid.

Hydrophobic monomeric residues can be charged or non-charged, generally. Some embodiments include neutral (non-charged) hydrophobic monomeric residues. In some embodiments, polymer chains can independently comprise a plurality of monomeric residues having a hydrophobic species selected from ($C_2$-$C_8$) alkyl, ($C_2$-$C_8$) alkenyl, ($C_2$-$C_8$) alkynyl, aryl, and heteroaryl (each of which may be optionally substituted). In certain embodiments, the plurality of monomeric residues can be derived from polymerization of ($C_2$-$C_8$) alkyl-ethacrylate, a ($C_2$-$C_8$) alkyl-methacrylate, or a ($C_2$-$C_8$) alkyl-acrylate (each of which may be optionally substituted).

Cationic monomeric residues can preferably comprise a deprotonatable cationic species. Considered in the aggregate, as incorporated into a polymer chain, such cationic monomeric residues can be substantially cationic at a pH of or greater than 7.0. Preferably, such cationic monomeric residues can have a pKa ranging from about 6.5 to about 9.0. Cationic monomeric residues can independently comprise a plurality of monomeric residues having a deprotonatable cationic species selected from the group consisting of acyclic amine, acyclic imine, cyclic amine, cyclic imine, and nitrogen-containing heteroaryl. Preferred cationic monomeric residues can be derived from polymerization of, in each case optionally substituted, (N,N-di(C1-C6)alkyl-amino(C1-C6) alkyl-ethacrylate, N,N-di(C1-C6)alkyl-amino(C1-C6)alkyl-methacrylate, or N,N-di(C1-C6)alkyl-amino(C1-C6)alkyl-acrylate.

Particularly preferred polymers or polymer chains can be block copolymer which can comprise or consist essentially of two or more blocks represented by formula I,

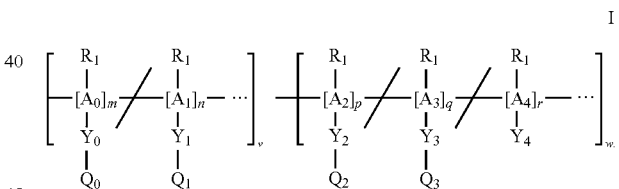

where
A0, A1, A2, A3 and A4 are each selected from the group consisting of —C—C—, —C—, —C(O)(C)aC(O)O—, —O(C)aC(O)— and —O(C)bO—,
a is an integer ranging from 1-4; and
b is an integer ranging from 2-4;
Y4 is selected from the group consisting of hydrogen, (1C-10C)alkyl, (3C-6C)cycloalkyl, O-(1C-10C) alkyl, —C(O)O(1C-10C)alkyl, C(O)NR6(1C-10C) and aryl, any of which is optionally substituted with one or more fluorine groups;
Y0, Y1 and Y2 are each independently selected from the group consisting of a covalent bond, (1C-10C)alkyl-, —C(O)O(2C-10C) alkyl-, —OC(O)(1C-10C)alkyl-, —O(2C-10C)alkyl- and —S(2C-10C)alkyl-1-C(O)NR6(2C-10C)alkyl-;
Y3 is selected from the group consisting of a covalent bond, (1C-10C)alkyl and (6C-10C)aryl; wherein tetravalent carbon atoms of A1-A4 that are not fully substituted with R1-R5 and Y0-Y4 are completed with an appropriate number of hydrogen atoms;

each R1, R2, R3, R4, R5, and R6 are independently selected from the group consisting of hydrogen, —CN, alkyl, alkynyl, heteroalkyl, cycloalkyl, heterocycloalkyl, aryl and heteroaryl, any of which may be optionally substituted with one or more fluorine atoms;

Q0 is a residue selected from the group consisting of residues which are hydrophilic at physiologic pH and are at least partially positively charged at physiologic pH (e.g., amino, alkylamino, ammonium, alkylammonium, guanidine, imidazolyl, pyridyl, or the like); at least partially negatively charged at physiologic pH but undergo protonation at lower pH (e.g., carboxyl, sulfonamide, boronate, phosphonate, phosphate, or the like); substantially neutral (or non-charged) at physiologic pH (e.g., hydroxy, polyoxylated alkyl, polyethylene glycol, polypropylene glycol, thiol, or the like); at least partially zwitterionic at physiologic pH (e.g., a monomeric residue comprising a phosphate group and an ammonium group at physiologic pH); conjugatable or functionalizable residues (e.g. residues that comprise a reactive group, e.g., azide, alkyne, succinimide ester, tetrafluorophenyl ester, pentafluorophenyl ester, p-nitrophenyl ester, pyridyl disulfide, or the like); or hydrogen;

Q1 is a residue which is hydrophilic at physiologic pH, and is at least partially positively charged at physiologic pH (e.g., amino, alkylamino, ammonium, alkylammonium, guanidine, imidazolyl, pyridyl, or the like); at least partially negatively charged at physiologic pH but undergoes protonation at lower pH (e.g., carboxyl, sulfonamide, boronate, phosphonate, phosphate, or the like); substantially neutral at physiologic pH (e.g., hydroxy, polyoxylated alkyl, polyethylene glycol, polypropylene glycol, thiol, or the like); or at least partially zwitterionic at physiologic pH (e.g., a monomeric residue comprising a phosphate group and an ammonium group at physiologic pH);

Q2 is a residue which is positively charged at physiologic pH, including but not limited to amino, alkylamino, ammonium, alkylammonium, guanidine, imidazolyl, and pyridyl;

Q3 is a residue which is negatively charged at physiologic pH, but undergoes protonation at lower pH, including but not limited to carboxyl, sulfonamide, boronate, phosphonate, and phosphate;

m is a number ranging from equal to 0 to less than 1.0 (e.g., 0 to about 0.49);

n is a number ranging from greater than 0 to 1.0 (e.g., about 0.51 to about 1.0);

the sum of (m+n)=1 p is a number ranging from about 0.1 to about 0.9 (e.g., about 0.2 to about 0.5);

q is a number ranging from about 0.1 to about 0.9 (e.g., about 0.2 to about 0.5);

r is a number ranging from 0 to about 0.8 (e.g., 0 to about 0.6);

the sum of (p+q+r)=1;

v ranges about 1 to about 25 kDa; and, w ranges from about 1 to about 50 kDa.

In some embodiments, the number or ratio of monomeric residues represented by p and q are within about 30% of each other, about 20% of each other, about 10% of each other, or the like. In specific embodiments, p is substantially the same as q. In certain embodiments, at least partially charged generally includes more than a trace amount of charged species, including, e.g., at least 20% of the residues are charged, at least 30% of the residues are charged, at least 40% of the residues are charged, at least 50% of the residues are charged, at least 60% of the residues are charged, at least 70% of the residues are charged, or the like.

In certain embodiments, m is 0 and Q1 is a residue which is hydrophilic and substantially neutral (or non-charged) at physiologic pH. In some embodiments, substantially non-charged includes, e.g., less than 5% are charged, less than 3% are charged, less than 1% are charged, or the like. In certain embodiments, m is 0 and Q1 is a residue which is hydrophilic and at least partially cationic at physiologic pH. In certain embodiments, m is 0 and Q1 is a residue which is hydrophilic and at least partially anionic at physiologic pH. In certain embodiments, m is >0 and n is >0 and one of and Q0 or Q1 is a residue which is hydrophilic and at least partially cationic at physiologic pH and the other of Q0 or Q1 is a residue which is hydrophilic and is substantially neutral at physiologic pH. In certain embodiments, m is >0 and n is >0 and one of and Q0 or Q1 is a residue which is hydrophilic and at least partially anionic at physiologic pH and the other of Q0 or Q1 is a residue which is hydrophilic and is substantially neutral at physiologic pH. In certain embodiments, m is >0 and n is >0 and Q1 is a residue which is hydrophilic and at least partially cationic at physiologic pH and Q0 is a residue which is conjugatable or functionalizable residues. In certain embodiments, m is >0 and n is >0 and Q1 is a residue which is hydrophilic and substantially neutral at physiologic pH and Q0 is a residue which is h conjugatable or functionalizable residues.

Exemplary but non-limiting polymers of this invention can be or comprise a polymer chain which is a random copolymer represented as compound 1, optionally with one or more counterions.

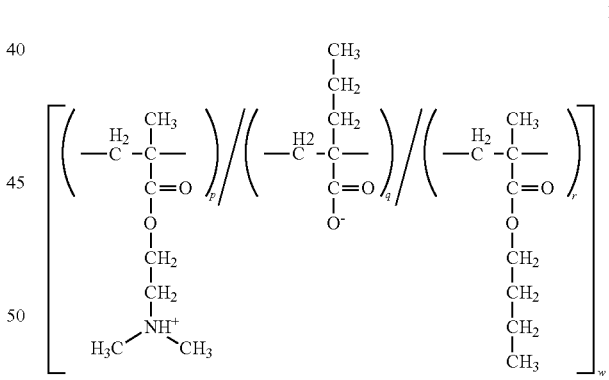

The constitutional units of compound 1 can be derived from the polymerizable monomers N,N-dimethylaminoethylmethacrylate (DMAEMA or "D"), propylacrylic acid (PAA or "P") and butyl methacrylate (BMA or "B"), represented respectively as follows:

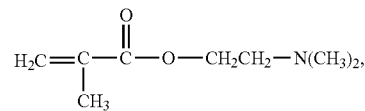

-continued

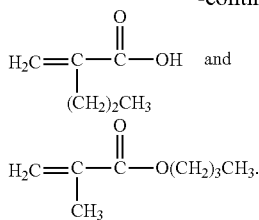

For the polymer chain represented by compound 1, p, q and r represent the mole fraction of each constitutional unit within the polymer chain, and can have the values described below.

The polymer can be a chain of compound 1, or can comprise a chain of compound 1 as one block of a block copolymer. For example, in one embodiment, the polymer can be a block copolymer comprising compound 1 as a membrane disrupting polymer block and one or more additional blocks. A diblock copolymer for example, can be represented by [A]v-[1]w where [A] represents a second block (e.g., a hydrophilic block or an amphiphilic block), and the letters v and w represent the molecular weight (number average) of the respective blocks in the copolymer.

For example, a polymer can comprise a block copolymer having two or more blocks, including blocks having a structure represented as follows (with appropriate counterions):

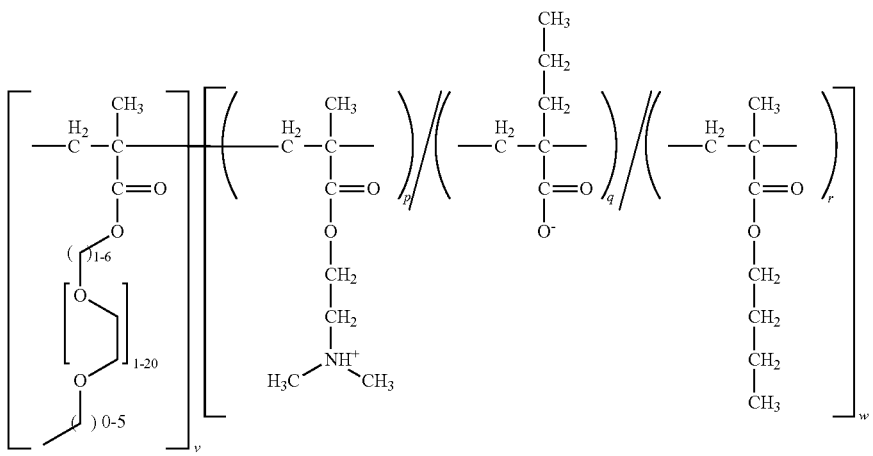

2

The constitutional units of compound 2 can be derived from the polymerizable monomers O—(C1-C6 alkyl)polyethyleneglycol-methacrylate (PEGMA) (first block as shown) and from the polymerizable monomers DMAEMA, PAA, and BMA as described above in connection with compound 1 (second block as shown). Letters p, q and r represent the mole fraction of each constitutional unit within the second block (as shown) and can have the values described below. The letters v and w represent the molecular weight (number average) of each block in the block copolymer and can have the values described below.

Particularly preferred polymers of the invention can comprise a block copolymer having two or more blocks, including blocks having a structure represented as:

$[DMAEMA]_v\text{-}[B_p\text{-}/\text{-}P_q\text{-}/\text{-}D_r]_w$     3

$[PEGMA]_v\text{-}[B_p\text{-}/\text{-}P_q\text{-}/\text{-}D_r]_w$     4

$[PEGMA_m\text{-}/\text{-}DMAEMA_n]_v\text{-}[B_p\text{-}/\text{-}P_q\text{-}/\text{-}D_r]_w$     5

$[PEGMA_m\text{-}/\text{-}MAA(NHS)_n]_v\text{-}[B_p\text{-}/\text{-}P_q\text{-}/\text{-}D_r]_w$     6

$[DMAEMA_m\text{-}/\text{-}MAA(NHS)_n]_v\text{-}[B_p\text{-}/\text{-}P_q\text{-}/\text{-}D_r]_w$     7

$[HPMA_m\text{-}/\text{-}PDSM_n]_v\text{-}[B_p\text{-}/\text{-}P_q\text{-}/\text{-}D_r]_w$     8

$[PEGMA_m\text{-}/\text{-}PDSM_n]_v\text{-}[B_p\text{-}/\text{-}P_q\text{-}/\text{-}D_r]_w$     9 where B is butyl methacrylate residue; P is propylacrylic acid residue; D, DMAEMA are each dimethylaminoethyl methacrylate residue; PEGMA is polyethyleneglycol methacrylate residue (e.g., with 1-20 ethylene oxide units, such as illustrated in compound 2, or 4-5 ethylene oxide units, or 7-8 ethylene oxide units); MAA(NHS) is methylacrylic acid-N-hydroxy succinimide residue; HPMA is N-(2-hydroxypropyl) methacrylamide residue; and PDSM is pyridyl disulfide methacrylate residue.

Generally, for each of the polymers comprising compounds 1 through 9, each of m, n, p, q, r, w and v are numbers. Preferably:

p is a number ranging from about 0.1 to about 0.9 (e.g., about 0.2 to about 0.5);

q is a number ranging from about 0.1 to about 0.9 (e.g., about 0.2 to about 0.5);

r is a number ranging from 0 to about 0.8 (e.g., 0 to about 0.6);

the sum of (p+q+r)=1;

v ranges about 5 to about 25 kDa; and, w ranges from about 5 to about 50 kDa.

In some specific embodiments, the ratio of w:v ranges from about 1:1 to about 5:1.

Polymers 1-9 are representative examples of polymers suitable for use in connection with the present invention. In certain priority applications, the polymer PRx0729v6 is used interchangeably with the polymer P7v6. Other polymers can also be used, including structurally related polymers (such as variations in molecular weights and/or monomeric residue ratios). In some embodiments, the constitutional unit(s) of the first block (as shown) are controlled to effect a first block (as shown) which is or comprises a constitutional unit that is neutral (e.g., PEGMA), cationic (e.g., DMAEMA), anionic (e.g., PEGMA-NHS, where the NHS is hydrolyzed to the acid, or acrylic acid), ampholytic (e.g., DMAEMA-NHS, where the NHS is hydrolyzed to the acid), or zwitterionic (for example, poly[2-methacryloyloxy-2' trimethylammonium-ethyl phosphate]). In some embodiments, polymers comprising pyridyl disulfide functionality in the first block (as shown), e.g., [PEGMA-PDSM]-[B-P-D], that can be and is optionally reacted with a thiolated biomolecular agent [such as a thiolated siRNA to form a polymer-siRNA conjugate].

Shielding/Solubilizing Agents

Generally, the various polymers (or polymer chains included as constituent moieties such as blocks of a block copolymer) of the compounds of the invention can comprise one or more shielding agent and/or solubilizing agent. The shielding agent can be effective for improving solubility of the polymer chain and can be effective for steric shielding of a therapeutic agent (e.g., polynucleotide, peptide, etc.). The shielding agent can also be effective for enhancing the stability of the therapeutic agent (e.g., polynucleotide or peptide, etc.) against enzymatic digestion in plasma. The shielding agent can also be effective for reducing toxicity of the certain compositions (e.g., compositions comprising polynucleotides). In some embodiments, the shielding agent can be a polymer comprising a plurality of neutral hydrophilic monomeric residues. The shielding polymer can be covalently coupled to a membrane destabilizing polymer, directly or indirectly, through an end group of the polymer or through a pendant functional group of one or more monomeric residues of the polymer. In some embodiments, a plurality of monomeric residues of the polymer chain can have a shielding species; preferably, such shielding species is a pendant moiety from a polymerizable monomer (from which the shielding monomeric residues are derived). For example, the polymer can comprise a plurality of monomeric residues having a pendant group comprising a shielding oligomer.

A preferred shielding/solubilizing polymer can be a polyethylene glycol (PEG) oligomer (e.g., having 20 or less repeat units) or polymer (e.g., having more than 20 repeat units). In certain embodiments, one block of a block copolymer can be or comprises a polyethylene glycol (PEG) oligomer or polymer—for example, covalently coupled to the alpha end or the omega end of the membrane destabilizing block of the copolymer. In another embodiment, a polyethylene glycol (PEG) oligomer or polymer can be covalently coupled to the polymer through a conjugating monomeric residue having a species which includes a functional group suitable for linking, directly or indirectly, to the polyethylene glycol oligomer or polymer. In another embodiment, the monomeric residue can be derived from a polymerizable monomer which includes a polyethylene glycol oligomer pendant to the monomer (e.g., PEGMA as described above).

In one general approach, PEG chains or blocks are covalently coupled to a membrane destabilizing polymer chain. For such embodiments, for example, PEG chains or blocks can have molecular weights ranging approximately from 1,000 to approximately 30,000. In some embodiments, the PEG is effective as (i.e., is incorporated into) a second block of a block copolymer. For example, PEG can be a second block coupled covalently to a block comprising a membrane destabilizing polymer. In some embodiments, PEG is conjugated to block copolymer ends groups, or to one or more pendant modifiable group present in polymeric compound, such as conjugated to modifiable groups within a hydrophilic segment or block (e.g., a second block) of a polymer (e.g., block copolymer). As an example, a block of a copolymer can be or can be conjugated to a shielding polymer having a repeat unit of Formula V

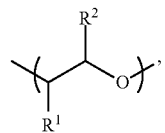

where $R^1$ and $R^2$ are each independently selected from the group consisting of hydrogen, halogen, hydroxyl, and optionally substituted $C_1$-$C_3$ alkyl, and having a molecular weight ranging from about 1,500 to about 15,000.

In another general approach, a monomeric residue is derived from a polymerizable monomer comprising a PEG oligomer; for example, such monomeric residues can be incorporated into the polymer or into one or more blocks of a block copolymer during polymerization. In preferred embodiments, monomeric residues can be derived from a polymerizable monomer having a pendant group comprising an oligomer of formula I

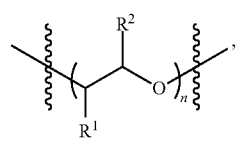

where $R^1$ and $R^2$ are each independently selected from the group consisting of hydrogen, halogen, hydroxyl, and optionally substituted $C_1$-$C_3$ alkyl, and n is an integer ranging from 2 to 20.

Polymerization

Generally, the various polymers (or polymer chains included as constituent moieties such as blocks of a block copolymer) of the compounds of the invention, can be prepared in any suitable manner. Suitable synthetic methods used to produce the polymers provided herein include, by way of non-limiting example, cationic, anionic and free radical polymerization.

Preferably the polymers as described above are prepared by the means of a free radical polymerization. When a free radical polymerization process is used, (i) the monomer, (ii) optionally desired co-monomer(s), and (iii) an optional source of free radicals are provided to trigger a free radical polymerization process. In some embodiments, the source of free radicals is optional because some monomers may self-initiate upon heating at high temperature, or photo-activated. In certain instances, after forming the polymerization mixture, the mixture is subjected to polymerization conditions. Polymerization conditions are conditions under which at least one monomer forms at least one polymer, as discussed herein. Such conditions are optionally varied to suitable levels and include, by way of non-limiting example, temperature, pressure, atmosphere, ratios of starting components used in the polymerization mixture and reaction time. The polymerization is performed neat or in any suitable solvent, and can be carried out in any suitable manner, including, e.g., in solution, dispersion, suspension, emulsion or bulk.

In some embodiments, initiators are present in the reaction mixture. Any suitable initiator is optionally utilized if useful in the polymerization processes described herein. Such initiators include, by way of non-limiting example, one or more of alkyl peroxides, substituted alkyl peroxides, aryl peroxides, substituted aryl peroxides, acyl peroxides, alkyl hydroperoxides, substituted alkyl hydroperoxides, aryl hydroperoxides, substituted aryl hydroperoxides, heteroalkyl peroxides, substituted heteroalkyl peroxides, heteroalkyl hydroperoxides, substituted heteroalkyl hydroperoxides, heteroaryl peroxides, substituted heteroaryl peroxides, heteroaryl hydroperoxides, substituted heteroaryl hydroperoxides, alkyl peresters, substituted alkyl peresters, aryl peresters, substituted aryl peresters, or azo compounds. In specific embodiments, benzoylperoxide (BPO) and/or AIBN are used as initiators.

In some embodiments, polymerization is effected using a controlled (living) radical polymerization process. In preferred embodiments, reversible addition-fragmentation chain transfer (RAFT) approaches are used in synthesizing polymers from ethylenic monomers. RAFT comprises a free radical degenerative chain transfer process. In some embodiments, RAFT procedures for preparing a polymer described herein employs a chain transfer agent (CTA).

Generally, polymers or polymer chains (e.g., polymer blocks) can be independently derived in a method comprising polymerizing in the presence of a reversible addition-fragmentation chain-transfer (RAFT) agent. Such RAFT agents can generally have the formula Y—RL, where RL is a leaving group, typically coupled to a chain-transfer moiety, Y, through a relatively weak covalent bond. Typically, Y can form a radical intermediate moiety, —Y.—, generated from or in the presence of a radical moiety (e.g., such as an initiator radical under initiation reaction conditions, or such as a propagating polymer chain radical, Pn, under radical polymerization conditions).

In generally preferred embodiments, the chain transfer agent (CTA) can comprise a thiocarbonylthio moiety. For example, the CTA can comprise a thiocarbonylthio moiety, —SC(=S)—, covalently bonded to an activating group, Z, and to a leaving group, —RL. Such CTA can be represented for example, by a compound having the formula RLSC(=S)Z. Various such RAFT chain-transfer agents are known for use in controlled (living) radical polymerizations, including various xanthates, dithiocarbamates, diothioesters and trithiocarbonates.). See for example, Moad et al., The Chemistry of Radical Polymerization, 2d Ed., Tables 9.10 to 9.18 at pp. 508 to 514, Elsevier (2006), which is incorporated herein by reference. In many embodiments, the chain transfer agent (CTA) can be a macromolecular chain transfer agent (macro-CTA). For example, a chain-transfer moiety, Y, of a RAFT chain transfer agent can be incorporated onto the ω-end of a polymer chain, Pn, to form a macro-CTA comprising a polymer compound, and represented by a formula Pn-Y. (In such case, the polymer chain, Pn, can effectively function as a leaving group, RL, of the macromolecular chain transfer agent.). As incorporated into a compound of the invention, —Y, is referred to as a chain transfer residue. Hence, in the context of compounds of the invention derived from radical polymerization, —Y can be a chain-transfer residue. The chain transfer residue can be derived from controlled (living) radical polymerization of under chain polymerization conditions. Such controlled radical polymerization reactions can be effected for example in the presence of a chain transfer agent (CTA) such as a RAFT agent (e.g., Y-RL) or such as a macro-CTA (e.g., Pn-Y). The chain-transfer residue, —Y, is typically covalently bonded to a polymer on the ω-end thereof (also referred to as the living end of the chain extension moiety when included in a macro CTA). The chain transfer residue, —Y, can preferably be a thiocarbonylthio moiety having a formula —SC(=S)Z, where Z is an activating group.

Various approaches are known for cleaving and/or derivatizing the chain transfer residue, Y, to form a chain transfer residue derivative. See for example, Moad et al., The Chemistry of Radical Polymerization, 2d Ed., pp. 538 to 539, Elsevier (2006), which is incorporated herein by reference. See also U.S. Pat. No. 6,619,409 to Charmot et al., which discloses cleavage of the thiocarbonylthio control transfer agent. Derivatized chain transfer residues, can be used for effectively coupling one or more biomolecular agents (such as one or more affinity reagents) to the polymer, optionally through a linking moiety.

Although RAFT agents are preferably employed, other controlled (living) radical polymerization methods are also suitable in connection with the invention. See for example, Moad et al., The Chemistry of Radical Polymerization, Elsevier (2006), which is incorporated herein by reference. In particular, atom transfer radical polymerization (ATRP) and stable free radical polymerization (SFRP) approaches are suitable. See Moad et al., Id.

Generally, polymers can have a low polydispersity index (PDI) or differences in chain length. Polydispersity index (PDI) can be determined in any suitable manner, e.g., by dividing the weight average molecular weight of the polymers by their number average molecular weight. Polydispersity values approaching one are achievable using radical living polymerization. Methods of determining molecular weight and polydispersity, such as, but not limited to, size exclusion chromatography, dynamic light scattering, matrix-assisted laser desorption/ionization chromatography and electrospray mass chromatography are well known in the art. In some embodiments, block copolymers of the polymeric compounds provided herein have a polydispersity index (PDI) of less than 2.0, or less than 1.5, or less than 1.4, or less than 1.3, or less than 1.2

Generally, polymerization processes described herein optionally occur in any suitable solvent or mixture thereof. Suitable solvents include water, alcohol(e.g., methanol, ethanol, n-propanol, isopropanol, butanol), tetrahydrofuran (THF) dimethyl sulfoxide (DMSO), dimethylformamide (DMF), acetone, acetonitrile, hexamethylphosphoramide, acetic acid, formic acid, hexane, cyclohexane, benzene, toluene, dioxane, methylene chloride, ether (e.g., diethyl ether), chloroform, and ethyl acetate. In one aspect, the solvent includes water, and mixtures of water and water-miscible organic solvents such as DMF.

Generally, polymerization processes described herein can be effected at temperature effective for the polymerization reaction. Temperatures can be varied based on and in consideration of other reaction aspects, including for example selections as to solvent, monomer (or comonomers) being polymerized (or copolymerized), chain transfer agent, heat transfer (exotherm control), reaction kinetics, and reaction thermodynamics. Typical temperature ranges can generally include a temperature ranging from about 2° C. to about 200° C., preferably from about 20° C. to about 110° C., and in some embodiments from about 40° C. to about 90° C., and or from about 50° C. to about 80° C.

Generally, polymerization processes described herein can be effected at a pressure effective for the polymerization reaction. Generally, reaction pressure is not narrowly critical, and can be at ambient pressure of about 1 atm or at higher pressures (e.g., ranging from 1 atm to about 10 atm) or a lower pressure (e.g., below 1 atm).

Generally, polymerization processes described herein can be effected under a reaction atmosphere effective for the polymerization reaction. For example, polymerization can be effected under an inert gas atmosphere (e.g., Ar, N2), or under ambient atmosphere.

Generally, polymerization processes described herein can be effected at various molar ratios of chain transfer agent (living chain transfer moieties or groups) to monomer effective for the polymerization reaction. For example, polymerization can be effected with a molar ratio of chain transfer agent (groups) to monomer ranging from about 1:1 to about 1:10,000, preferably from about 1:5 to about 1:5000, and most preferably from about 1:10 to about 1:2000In some embodiments, sch molar ratio can range from about 1:10 to about 1:1500.

Generally, polymerization processes described herein can be effected at concentrations of monomer(s) in the solvent ranging from about 5% to about 95% by weight, preferably from about 10% to about 90% solids, by weight, and in some embodiments, from about 20% to about 80% solids, by weight, in each case relative to total weight of solution.

Generally, polymerization processes described herein can be effected at various molar ratios of chain transfer agent (living chain transfer moieties or groups) to initiator effective for the polymerization reaction. For example, polymerization can be effected with a molar ratio of chain transfer agent (groups) to initiator ranging from about 1:2 to about 50:1, and preferably from about 1:1 to about 40:1, and in some embodiments from about 2:1 to about 30:1.

Generally, polymerization processes described herein can be effected for various reaction times effective for the polymerization reaction. For example, the polymerization can be effected over a reaction time period ranging from about 0.5 hr to about 96 hr, preferably from about 1 hour to about 72 hours, more preferably from about 1 hour to 36 hours, and in some embodiments from about 2 hours to 24 hours, or from about 3 hours to about 12 hours.

Generally, the aforementioned aspects and other factors known in the art can be used to effect the polymerization reaction of interest. See generally, for example, Moad et al., The Chemistry of Radical Polymerization, 2d Ed., Elsevier (2006), which is incorporated herewith in this regard.

The polymer may be chemically conjugated to the bispecific affinity reagent by any standard chemical conjugation technique. The covalent bond between the polymer and the bispecific affinity reagent may be non-cleavable, or cleavable bonds may be used. Particularly preferred cleavable bonds are disulfide bonds that dissociate in the reducing environment of the cytoplasm. Covalent association is achieved through chemical conjugation methods, including but not limited to amine-carboxyl linkers, amine-sulfhydryl linkers, amine-carbohydrate linkers, amine-hydroxyl linkers, amine-amine linkers, carboxyl-sulfhydryl linkers, carboxyl-carbohydrate linkers, carboxyl-hydroxyl linkers, carboxyl-carboxyl linkers, sulfhydryl-carbohydrate linkers, sulfhydryl-hydroxyl linkers, sulfhydryl-sulfhydryl linkers, carbohydrate-hydroxyl linkers, carbohydrate-carbohydrate linkers, and hydroxyl-hydroxyl linkers. Conjugation can also be performed with pH-sensitive bonds and linkers, including, but not limited to, hydrozone and acetal linkages. A large variety of conjugation chemistries are established in the art (see, for example, Bioconjugation, Aslam and Dent, Eds, Macmillan, 1998 and chapters therein). Alternatively, conjugation can be achieved using standard coordination chemistry, such as by way of a platinum complex that forms coordinate bonds with proteinaceous entities. See, e.g., U.S. Pat. No. 5,985,566.

The bispecific polymer delivery vehicle can be used to deliver its second affinity reagent into cells, either for in vitro use, as a research reagent, or in mice or other small animal as a research reagent. Such reagents would be useful in target validation, to show that inhibition of a particular target has particularly favorable efficacy in cells, or to characterize and study side-effect or toxicity profiles that result from inhibition of chosen targets. The bispecific polymer delivery vehicle compositions may also be used as therapeutics, to inhibit the action, or to stimulate the action, of specific proteins in humans and thereby achieve a desirable therapeutic outcome to influence a disease state. In addition, the compositions of the present invention may be used as diagnostics for the assessment of disease states in humans.

Bispecific polymer delivery vehicles may be formulated in any one of a variety of excipients and delivered by any route, including but not limited to intravenous, intratumoral, intraocular, by inhalation, orally, subcutaneously, intracranially, or by a catheter, pump or other device.

Cellular signaling proteins form the basis of cell behavior, and the ability to intervene in selected signaling pathways would be desirable to treat a variety of disease states. Diseases that may be influenced by the compositions and methods of the present invention include but are not limited to cancer, either via targeting the cancer cells themselves or targeting endothelial cells to inhibit tumor neovascularization or through targeting tumor stromal cells; autoimmune diseases; inflammation; wound healing; atherosclerosis; osteoarthritis; CNS disorders; and metabolic disorders such as diabetes and obesity.

In some embodiments, polymeric carriers of the present invention have superior commercial viability relative to other technologies for delivering polynucleotides, including but not limited to: decreased immunogenicity of the carrier following repeat in vivo administration; fewer steps needed to assemble the multiple elements of the delivery vehicle, resulting in lower cost of goods; and reproducibility of manufacture, as judged by the ability to manufacture repeated batches of product with less than 5%, 10%, or 20% variability in biophysical assay results (such as GPC, DLS, TEM) between batches.

Abbreviations

Throughout the description of the present invention, various known acronyms and abbreviations are used to describe monomers or monomeric residues derived from polymerization of such monomers. Without limitation, unless otherwise noted: "BMA" (or the letter "B" as equivalent shorthand notation) represents butyl methacrylate or monomeric residue derived therefrom; "DMAEMA" (or the letter "D" as equivalent shorthand notation) represents N,N-dimethylaminoethyl methacrylate or monomeric residue derived therefrom; "Gal" refers to galactose or a galactose residue, optionally including hydroxyl-protecting moieties (e.g., acetyl) or to a pegylated derivative thereof (as described below); HPMA represents 2-hydroxypropyl methacrylate or monomeric residue derived therefrom; "MAA" represents methylacrylic acid or monomeric residue derived therefrom; "MAA(NHS)" represents N-hydroxyl-succinimide ester of methacrylic acid or monomeric residue derived therefrom; "PAA" (or the letter "P" as equivalent shorthand notation) represents 2-propylacrylic acid or monomeric residue derived therefrom, "PEGMA" refers to the pegylated methacrylic monomer, $CH_3O(CH_2O)_{7-8}OC(O)C(CH_3)CH_2$ or monomeric residue derived therefrom. In each case, any such designation indicates the monomer (including all salts, or ionic analogs thereof), or a monomeric residue derived from polymerization of the monomer (including all salts or ionic analogs thereof), and the specific indicated form is evident by context to a person of skill in the art.

The following Examples are for illustration purposes and are not to be construed as limiting the invention

EXAMPLE 1

Construction of a Ras Bispecific Polymer Delivery Vehicle

The first affinity reagent, OKT 9, is a monoclonal antibody against the human type 1 transferrin receptor and is available from ATCC(CRL 8021 C). The hybridoma is cultured, expanded and the secreted monoclonal antibody harvested and purified using protein A or G chromatography (Antibody Engineering: A Practical Approach, McCafferty, Hoogenboom and Chiswell Eds, IRL Press 1996).

The second affinity reagent, Y13-259, is a monoclonal antibody against the ras protein (Furth et al., 1982) and is obtained as a hybridoma from ATCC(CRL 1742). The hybridoma is cultured, expanded and the secreted monoclonal antibody harvested and purified using protein A or G chromatography (Antibody Engineering: A Practical Approach, McCafferty, Hoogenboom and Chiswell Eds, IRL Press 1996).

The first and second affinity reagents are co-conjugated to poly(propylacrylic acid) (PAA)-co-pyridyl disulfide acrylate (PDSA), p(PAA-co-PDSA), via disulfide exchange between the PDSA component of the polymer and free thiols introduced onto the antibody by reaction with Traut's reagent (2-iminothiolane, Pierce Biotechnology, Rockford, Ill.). 10 mg of antibody is mixed with a 10× molar excess of Traut's reagent in conjugation buffer (0.1 M phosphate buffer, pH 7.8, 0.15 M NaCl, 5 mM EDTA) for 1 hour at room temperature. The reaction mixture is purified using a PD-10 desalting column containing Sephadex G-25 (MWCO 5 kD, GE Healthcare, Piscataway, N.J.) and the degree of modification is estimated by Ellman's assay (Pierce Biotechnology, Rockford, Ill.). For this assay, 2.5× molar excess of p(PAA-co-PDSA) is immediately added to the modified protein and allowed to react 2 hours at room temperature in conjugation buffer. The degree of conjugation is estimated by measuring the absorbance at 343 nm ($A_{343}$) of the pyridine-2-thione group released from PDSA upon disulfide exchange. After conjugation, the conjugate is purified using gel permeation chromatography (GPC).

For the synthesis of p(PAA-co-PDSA), 0.007 mol PAA (Gateway Chemical Technology, St. Louis, Mo.), 0.00011 mol PDSA, and 0.000056 mol free-radical initiator azobisisobutyronitrile (AIBN, purified by recrystallization from methanol) are combined in a 5 ml flask and degassed by 4 rounds of freeze-vacuum-thaw then reacted at 60° C. for 24 hours. The polymer is dissolved in 3 ml dimethyl formamide (DMF) and purified by 3 rounds of precipitation in 500 ml diethyl ether. Polymer compositions are determined by $H^1$-NMR using a Bruker AVance 300 MHz instrument and deuterated dimethyl sulfoxide (DMSO-d6, Fisher Chemical, Pittsburgh, Pa.). PDSA content is determined both by NMR and by the absorbance at 343 nm of pyridine-2-thione released from the polymer following reduction with excess of dithiothreitol (DTT). The molecular weight distribution is determined by GPC (Viscotek VE2001 sample module, VE3580 RI Detector, Waters Corp. ultrahydrogel columns) in 0.1 M sodium phosphate buffer, pH 8 using poly(ethylene oxide) (PEO) standards (Polysciences, Inc., Warrington, Pa.).

EXAMPLE 2

Demonstration of Activity of a Ras Bispecific Polymer Delivery Vehicle

The HT1080 cell line (available from ATCC), harboring an activated N-ras gene, is cultured in DMEM with 10% FCS and antibiotics at 37 degrees centigrade in a humidified atmosphere of 10% carbon dioxide in air. Cells are expanded, plated at a density of 100,000 cells per 60 mm plastic cell culture Petri dish in 5 ml liquid cultures, incubated for 15-18 h, then exposed to 0, 1, 10, 50 and 200 ug/ml of the bispecific polymer delivery vehicle for 8 h. Cells are then removed from the plastic with trypsin/EDTA, centrifuged, resuspended in culture media, counted using a hemacytometer, and seeded at a density of 20,000 cells/ml in culture media as above, but containing the same concentrations of the bispecific polymer delivery vehicle and 0.3% agar in 60 mm Petri dishes (5 ml/dish).

Cell cultures are incubated for 14 days at 37 degrees centigrade in a humidified atmosphere of 10% carbon dioxide in air. The cultures are then scored by counting the number of agar colonies per plate, in comparison to control cultures.

EXAMPLE 3

Construction of a p53 Bispecific Polymer Delivery Vehicle

The first affinity reagent is the OKT 9 antibody described above in Example 1. The second affinity reagent, PAb421, is a monoclonal antibody (Harlow et al, 1981) directed against the carboxyl terminus of human p53 protein, and can rescue the transcriptional defects of the p53 mutant present in SW480 colorectal carcinoma cells (Selivanova et al., 1997). PAb421 is obtained as a hybridoma. The hybridomas expressing the first and second affinity reagents are cultured, expanded and the secreted monoclonal antibody harvested and purified using a protein A or G column as described above in Example 1.

The first and second affinity reagents are then co-conjugated to the p(PAA-co-PDSA) polymer and purified as described above in Example 1.

EXAMPLE 4

Demonstration of Activity of p53 Bispecific Polymer Delivery Vehicle

SW480 cells are obtained from ATTC (CCL-228). Cells are grown in DMEM with 10% FCS and antibiotics at 37 degrees centigrade in a humidified atmosphere of 10% carbon dioxide in air. Cells are expanded to near-confluency, plated at a density of 500,000 cells per 100 mm plastic cell culture Petri dish in 15 ml liquid cultures, incubated for 15-18 h, then transfected using LipofectAMINE (Invitrogen, Carlsbad, Calif.) according to the manufacturers recommendations with 2 ug of the expression plasmid PG-13 CAT (Kern et al., 1992). Cells are incubated and exposed to 0, 1, 10, 50 and 200 ug/ml of the bispecific polymer delivery vehicles in liquid culture for 48 h, then harvested and assayed for chloramphenicol acetyltransferase (CAT) activity. Cell lysates are prepared by 3 cycles of freeze-thawing, and the cleared supernatant is assayed for CAT activity using a standard 14-C chloramphenicol thin-layer chromatography assay, in comparison to control cultures.

EXAMPLE 5

Creation and Demonstration of Activity of a Ras Bispecific Polymer Delivery Vehicle Using a Bispecific Fusion Protein The bispecific affinity reagent in this example is a bispecific antibody. The first and second affinity reagents are assembled from recombinant DNA clones by standard recombinant and PCR techniques. The first affinity reagent is derived from the monoclonal antibody hybridoma OKT 9 directed against the transferrin receptor, and the second affinity reagent is derived from the ras antibody from the hybridoma Y13-259, both described above in Example 1. mRNA is isolated from the respective hybridoma cells, reverse-transcribed into cDNA using antisense oligo-dT or gene-specific primers, and cloned into a plasmid vector. Clones are sequenced and characterized. They are then engineered according to standard protocols to combine the heavy and light chains of each antibody, separated by a short peptide linker, into a bacterial or mammalian expression vector as previously described, and expressed and purified according to well-established protocols in mammalian cells (Kufer et al., 2004; Antibody Engineering: A Practical Approach, McCafferty, Hoogenboom and Chiswell Eds, IRL Press 1996). The resulting bispecific affinity reagent thus binds to the transferrin receptor cell surface antigen, and to the ras intracellular target.

The bispecific scFv fragment is then cloned into a mammalian expression vector, and the vector transfected into CHO cells. The CHO cells are screened for productivity of the scFv, and the resulting cells used to express the bispecific scFv, which is then harvested and purified by standard chromatographic techniques (see Antibody Engineering: A Practical Approach, McCafferty, Hoogenboom and Chiswell Eds, IRL Press 1996).

The purified bispecific scFv is then conjugated to the p(PAA-co-PDSA) polymer and purified as described above in Example 1, and assayed for activity as described above in Example 2.

EXAMPLE 6

Creation and Demonstration of Activity of a p53 Bispecific Polymer Delivery Vehicle Using a Bispecific Fusion Protein The bispecific affinity reagent in this example is a bispecific antibody. The first and second affinity reagents are assembled from recombinant DNA clones by standard recombinant and PCR techniques. The first affinity reagent is derived from the monoclonal antibody hybridoma OKT 9 directed against the transferrin receptor, and the second affinity reagent is derived from the p53 antibody from the hybridoma PAb421, both described above in Examples 1 and 3. mRNA is isolated from the respective hybridoma cells, reverse-transcribed into cDNA using antisense oligo-dT or gene-specific primers, and cloned into a plasmid vector. Clones are sequenced and characterized. They are then engineered according to standard protocols to combine the heavy and light chains of each antibody, separated by a short peptide linker, into a bacterial or mammalian expression vector as previously described, and expressed and purified according to well-established protocols in mammalian cells (Kufer et al., 2004; Antibody Engineering: A Practical Approach, McCafferty, Hoogenboom and Chiswell Eds, IRL Press 1996). The resulting bispecific affinity reagent thus binds to the transferrin receptor cell surface antigen, and to the p53 intracellular target.

The bispecific scFv fragment is then cloned into a mammalian expression vector, and the vector transfected into CHO cells. The CHO cells are screened for productivity of the scFv, and the resulting cells used to express the bispecific scFv, which is then harvested and purified by standard chromatographic techniques (see Antibody Engineering: A Practical Approach, McCafferty, Hoogenboom and Chiswell Eds, IRL Press 1996).

The purified bispecific scFv is then conjugated to the p(PAA-co-PDSA) polymer and purified as described above in Example 1, and assayed for activity as described above in Example 4.

In the following examples, a novel diblock copolymer carrier is described that facilitates intracellular delivery of a bispecific peptide containing two functional domains, connected by direct polymer-peptide conjugation: (1) a cell binding and endocytotic update domain (the protein transduction domain, penetratin) and (2) a pro-apoptotic Bak-BH3 peptide with pharmaceutical properties. The polymer was prepared using reversible addition fragmentation chain transfer (RAFT) (Chiefari et al. Macromolecules. 1998; 31(16):5559-5562) to form an end-functionalized, modular diblock copolymer that incorporates an N-(2-hydroxypropyl) methacrylamide (HPMA) first block to enhance water solubility and favorable pharmacokinetic properties and a pH-responsive polymer block composed of dimethylaminoethyl methacrylate (DMAEMA), propylacrylic acid (PAA), and butyl methacrylate (BMA) that provides a mechanism for peptide endosomal escape. This polymeric carrier was conjugated to the bi-specific peptide via a reducible disulfide bond that ensures polymer release of the peptide upon delivery to the cytosol. The polymer exhibits pH-dependent membrane destabilizing behavior, and peptide-polymer conjugation was shown to significantly enhance peptide intracellular delivery and downstream pro-apoptotic bioactivity. The results show that this multifunctional diblock polymer carrier demonstrates the delivery of a peptide drug to an intracellular target.

EXAMPLE 7

Functional Design of Poly[HPMA]-b-[(PAA)(BMA)(DMAEMA)]

FIG. 1 shows the polymer design for Poly[HPMA]-b-[(PAA)(BMA)(DMAEMA)]. Multifunctional properties were incorporated via RAFT polymer synthesis strategies using a pyridyl disulfide end-functionalized CTA to form a diblock architecture designed to possess aqueous solubility and pH-dependent membrane destabilizing properties. The monomer chemical functionalities highlighted in FIG. 1 were chosen in order to produce the desired properties for each polymer block. Importantly, module 3 was designed to be near charge neutrality at physiologic pH (approximately 50% DMAEMA protonation and 50% PAA deprotonation predicted) and to undergo a transition to a more hydrophobic and positively charged state in lower pH environments.

EXAMPLE 8

Preparation of Thiol Reactive Polymer: Synthesis of Trithiocarbonic acid 1-cyano-1-methyl-3-[2-(pyridin-2-yldisulfanyl)-ethylcarbamoyl]-propyl ester ethyl ester (PyrECT)

Figure 2:
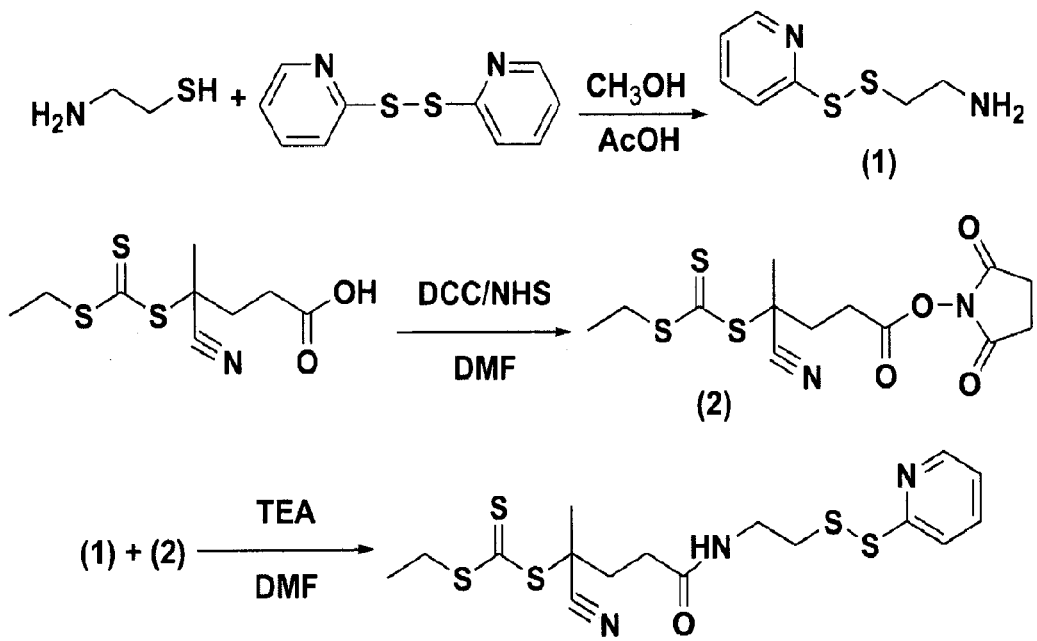
FIG. 2 illustrates the synthesis of a chain transfer agent according to an embodiment of the present invention.

The 4-cyano-4-(ethylsulfanylthiocarbonyl)sulfanylpentanoic acid (ECT) precursor was synthesized as shown in FIG. 2. The pyridyl disulfide functionalized RAFT chain transfer agent (CTA) was synthesized by first converting ECT to the NHS ester followed by reaction with pyridyldithioethylamine.

ECT (1.05 g, 4 mmol) and N-hydroxysuccinimide (0.460 g, 4 mmol) were dissolved in 100 mL of chloroform. The mixture was then cooled to 0° C. at which time N,N'-dicyclohexylcarbodiimide (0.865 mg, 4.2 mmol) was added. The solution was maintained at 0° C. for 1 hour and then allowed to react at room temperature for 22 hours. The solution was then filtered to remove the dicyclohexyl urea and the solution concentrated via rotary evaporation. The resultant solid was then dried under vacuum and used without any further purification. NHS ECT (1.80 g, 5.0 mmol) and pyridyldithioethylamine (0.90 g, 5.0 mmol) where then separately dissolved in 200 and 300 mL of chloroform, respectively. The solution of pyridyldithio-ethylamine was then added dropwise as three fractions 20 minutes apart. The mixture was then allowed to react at room temperature for 2 hours. After solvent removal, two successive column chromatographies (Silica gel 60, Merk) were performed (ethyl acetate:hexane 50:50; ethyl acetate:hexane 70:30 v/v) yielding a viscous orange solid. 1H NMR 200 MHz (CDCl3, RT, ppm) 1.29-1.41 [t, CH3CH2S: 3H], 1.85-1.93 [s, $(CH_3)C(CN)$: 3H], 2.33-2.59 [m, $C(CH_3)(CN)(CH_2CH_2)$: 4H], 2.86-2.97 [t, $CH_2SS$: 2H], 3.50-3.61 [t, $NHCH_2$: 2H], 7.11-7.22 [m, Ar Para CH: 1H], 7.46-7.52 [m, Ar CH Ortho: 1H], 7.53-7.62 [br, NH: 1H], 7.53-7.68 [m, Ar meta CH: 1H], 8.47-8.60 [m, meta CHN, 1H].

Preparation of Thiol Reactive Polymer: Raft Polymerization of Pyridyl Disulfide Functionalized poly[HPMA]-b-[(PAA)(BMA)(DMAEMA)]

The RAFT polymerization of N-(2-hydroxypropyl) methacrylamide (HPMA) was conducted in methanol (50 weight percent monomer:solvent) at 70° C. under a nitrogen atmosphere for 8 hours using 2,2'-azo-bis-isobutyrylnitrile (AIBN) as the free radical initiator. The molar ratio of CTA to AIBN was 10 to 1 and the monomer to CTA ratio was set so that a molecular weight of 25,000 g/mol would be achieved if at 100% conversion. The poly(HPMA) macro-CTA was isolated by repeated precipitation into diethyl ether from methanol.

The macro-CTA was dried under vacuum for 24 hours and then used for block copolymerization of dimethylaminoethyl methacrylate (DMAEMA), propylacrylic acid (PAA), and butyl methacrylate (BMA). Equimolar quantities of DMAEMA, PAA, and BMA ($[M]_o/[CTA]_o$=250) were added to the HPMA macroCTA dissolved in N,N-dimethylformamide (25 wt % monomer and macroCTA to solvent). The radical initiator V70 was added with a CTA to initiator ratio of 10 to 1. The polymerization was allowed to proceed under a nitrogen atmosphere for 18 hours at 30° C. Afterwards, the resultant diblock polymer was isolated by precipitation 4 times into 50:50 diethyl ether/pentane, redissolving in ethanol between precipitations. The product was then washed 1 time with diethyl ether and dried overnight in vacuo.

Gel permeation chromatography (GPC) was used to determine molecular weight and polydispersity (Mw/Mn, PDI) of both the poly(HPMA) macroCTA and the diblock copolymer in DMF. Molecular weight calculations were based on column elution times relative to polymethyl methacrylate standards using HPLC-grade DMF containing 0.1 wt % LiBr at 60° C. as the mobile phase. Tris(2-carboxyethyl) phosphine hydrochloride (TCEP) was used to reduce the polymer end pyridyl disulfide, releasing 2-pyridinethione. Based on the experimentally determined polymer molecular weight and the molar extinction coefficient of 2-pyridinethione at 343 nm ($8080 M^{-1}cm^{-1}$) in aqueous solvents, percent end group preservation was determined for the poly(HPMA) macroCTA and the diblock copolymer.

EXAMPLE 9

Polymer-Peptide Conjugation

Fusion with the peptide transduction domain peptide transporting (also know as the Antennapedia peptide (Antp) sequence was utilized to synthesize a cell internalizing form of the Bak-BH3 peptide (Antp-BH3) containing a carboxy-terminal cysteine residue (NH2-RQIKIWFQNRRMKWKK-MGQVGRQLAIIGDDINRRYDSC—COOH). To ensure free thiols for conjugation, the peptide was reconstituted in water and treated for 1 hour with the disulfide reducing agent TCEP immobilized within an agarose gel. The reduced peptide (400 µM) was then reacted for 24 hours with the pyridyl disulfide end-functionalized polymer in phosphate buffer (pH 7) containing 5 mM ethylenediaminetetraacetic acid (EDTA).

Figure 3:
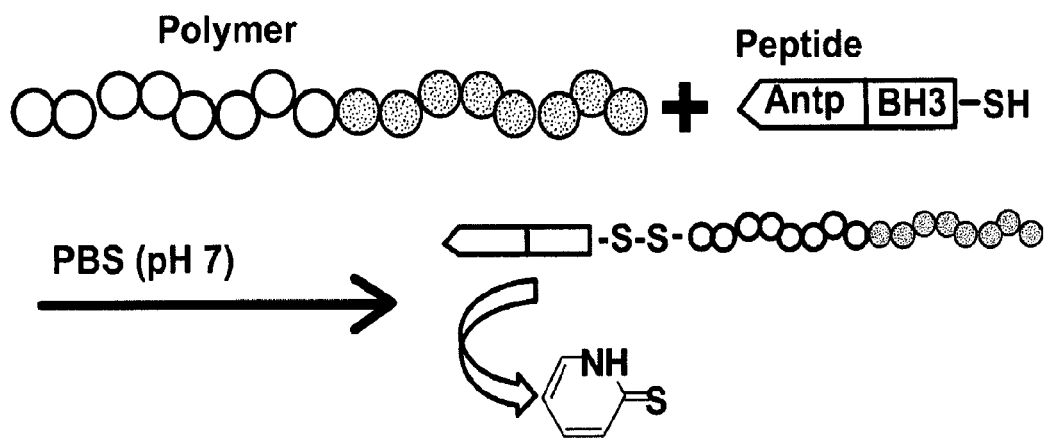
FIG. 3 illustrates the linking of a bispecific affinity reagent to a pH-responsive membrane destabilizing polymer according to an embodiment of the present invention.

As shown in FIG. 3, reaction of the pyridyl disulfide polymer end group with the peptide cysteine creates 2-pyridinethione, which can be spectrophotometrically measured to characterize conjugation efficiency. To further validate disulfide exchange, the conjugates were run on an SDS-PAGE 16.5% tricine gel. In parallel, aliquots of the conjugation reactions were treated with immobilized TCEP prior to SDS-PAGE to verify release of the peptide from the polymer in a reducing environment.

Conjugation reactions were conducted at polymer/peptide stoichiometries of 1, 2, and 5. UV spectrophotometric absorbance measurements at 343 nm for 2-pyridinethione release indicated conjugation efficiencies of 40%, 75%, and 80%, respectively (moles 2-pyridinethione/moles peptide). An SDS PAGE gel was utilized to further characterize peptide-polymer conjugates. At a polymer/peptide molar ratio of 1, a detectable quantity of the peptide formed dimers via disulfide bridging through the terminal cysteine. However, the thiol reaction to the pyridyl disulfide was favored, and the free peptide band was no longer visible at polymer/peptide ratios equal to or greater than 2 (FIG. 4A). By treating the conjugates with the reducing agent TCEP, it was possible to cleave the polymer-peptide disulfide linkages as indicated by the appearance of the peptide band in these samples (FIG. 4B).

EXAMPLE 10 pH-dependent Membrane Destabilizing Properties of poly[HPMA]-b-[(PAA)(BMA)(DMAEMA)]

In order to assess the polymer's potential for endosomolytic activity, a membrane disruption assay was utilized to measure the capacity of the polymer to trigger pH-dependent disruption of lipid bilayer membranes as shown in FIG. 5. Whole human blood was drawn and centrifuged for plasma removal. The remaining erythrocytes were washed three times with 150 mM NaCl and resuspended into phosphate buffers corresponding to physiological (pH 7.4), early endosome (pH 6.6), and late endosome (pH 5.8) environments. The polymer (1-40 µg/mL) or 1% Triton X-100 was added to the erythrocyte suspensions and incubated for 1 hour at 37° C. Intact erythrocytes were pelleted via centrifugation, and the hemoglobin content within the supernatant was measured via absorbance at 541 nm. Percent hemolysis was determined relative to Triton X-100. Polymer hemolysis was quantified at concentrations ranging from 1-40 µg/mL relative to 1% v/v Triton X-100. This experiment was completed 2 times in triplicate, yielding similar results. The data shown represent a single experiment conducted in triplicate±standard deviation.

Red blood cell hemolysis measures pH-dependent membrane disruption properties of the diblock copolymer at pH values mimicking physiologic (7.4), early endosomal (6.6) and late endosomal (5.8) environments. At physiologic pH, no significant red blood cell membrane disruption was observed even at polymer concentrations as high as 40 µg/mL (FIG. 5). However, as the pH was lowered to endosomal values, a significant increase in hemolysis was detected, with greater membrane disruption at pH 5.8 compared to 6.6. The hemolytic behavior of the polymer correlated to polymer concentration, with nearly 70% erythrocyte lysis occurring at 40 µg/mL polymer in pH 5.8 buffer. This sharp "switch" to a membrane destabilizing conformation at endosomal pH combined with negligible membrane activity in the physiologic pH range indicates potential for this polymer as a non-toxic intracellular delivery vehicle.

EXAMPLE 11

Characterization of Intracellular Delivery in HeLa Cells

HeLas, human cervical carcinoma cells (ATCC CCL-2), were maintained in minimum essential media (MEM) containing L-glutamine, 1% penicillin-streptomycin, and 10% FBS. Prior to experiments, HeLas were allowed to adhere overnight in 8-well chamber slides (20,000 cells/well) for microscopy or 96-well plates (10,000 cells/well) for other assays. Polymer-peptide conjugates and controls were added in MEM with 1% FBS.

Polymer intracellular delivery potential was evaluated following bioconjugation to the Bak-BH3 peptide fused with the Antp (penetratin) cell penetrating peptide. BH3 fusion to Antp has been extensively studied as a cell translocation domain and has previously been found to trigger apoptotic signaling (Li et al. Neoplasia (New York, N.Y. 2007; 9(10): 801-811). However, it is believed that therapeutics delivered via peptidic transduction domains may suffer from hindered potency due to sequestration within intracellular vesicles (Sugita et al. British Journal of Pharmacology. 2008; 153(6): 1143-1152).

The following in vitro studies demonstrate that the combined Antp-BH3 peptide cytoplasmic delivery and pro-apoptotic functionality was enhanced by conjugation to the diblock polymer.

Microscopic Analysis of Conjugate Endosomal Escape

An amine reactive Alexa-488 succinimidyl ester was mixed at a 1 to 1 molar ratio with the Antp-BH3 peptide in anhydrous dimethyl formamide (DMF). Unreacted fluorophore and organic solvent were removed using a PD10 desalting column, and the fluorescently labeled peptide was lyophilized. Alexa-488 labeled Antp-BH3 was conjugated to the polymer as described above. Free peptide or polymer-peptide conjugate was applied to HeLas grown on chambered microscope slides at a concentration of 25 µM Antp-BH3. Cells were treated for 15 minutes, washed twice with PBS, and incubated in fresh media for an additional 30 minutes. The samples were washed again and fixed with 4% paraformaldehyde for 10 minutes at 37° C. Slides were mounted with ProLong Gold Antifade reagent containing DAPI and imaged using a fluorescent microscope.

Figure 6A:
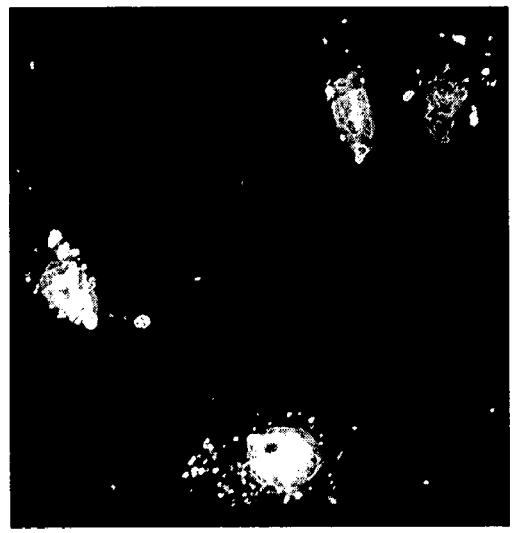
FIGS. 6A and 6B depict the results of fluorescent microscopic analysis of peptide delivery to cells via a prior art composition and a composition according to an embodiment of the present invention.
Figure 6B:

To study the effects of polymer conjugation on peptide endosomal escape, the Alexa-488 labeled peptide was analyzed by fluorescent microscopy. The fluorescently labeled peptide was delivered alone or as the polymer bioconjugate. Microscopic analysis revealed clear differences in peptide intracellular localization following polymer conjugation (FIGS. 6A and 6B). The peptide alone displayed punctate staining, indicative of endosomal compartmentalization. Samples delivered polymer-peptide conjugate exhibited a dispersed fluorescence pattern, consistent with peptide diffusion throughout the cytoplasm. Representative images illustrating (FIG. 6A) punctate peptide staining in the samples delivered peptide alone and (FIG. 6B) dispersed peptide fluorescence within the cytosol following delivery of peptide-polymer conjugate. Samples were treated for 15 minutes with 25 µM peptide and prepared for microscopic examination following DAPI nuclear staining.

Measurement of Conjugate Cytotoxicity

Bioconjugate efficacy for triggering tumor cell death was determined using a lactate dehydrogenase (LDH) cytotoxicity assay. At the end of each time point, cells were washed two times with PBS and then lysed with cell lysis buffer (100 µL/well, 20 mM Tris-HCl, pH 7.5, 150 mM NaCl, 1 mM $Na_2EDTA$, 1 mM EGTA, 1% Triton, 2.5 mM sodium pyrophosphate, 1 mM 13-glycerophosphate, 1 mM sodium orthovanadate) for 1 hour at 4° C. 20 µl of lysate from each sample was diluted into 80 µl PBS, and LDH was quantified by mixing with 100 µL of the LDH substrate solution. Following a 10 minute incubation, LDH was determined by measuring absorbance at 490 nm. Percent viability was expressed relative to samples receiving no treatment.

Figure 7A:
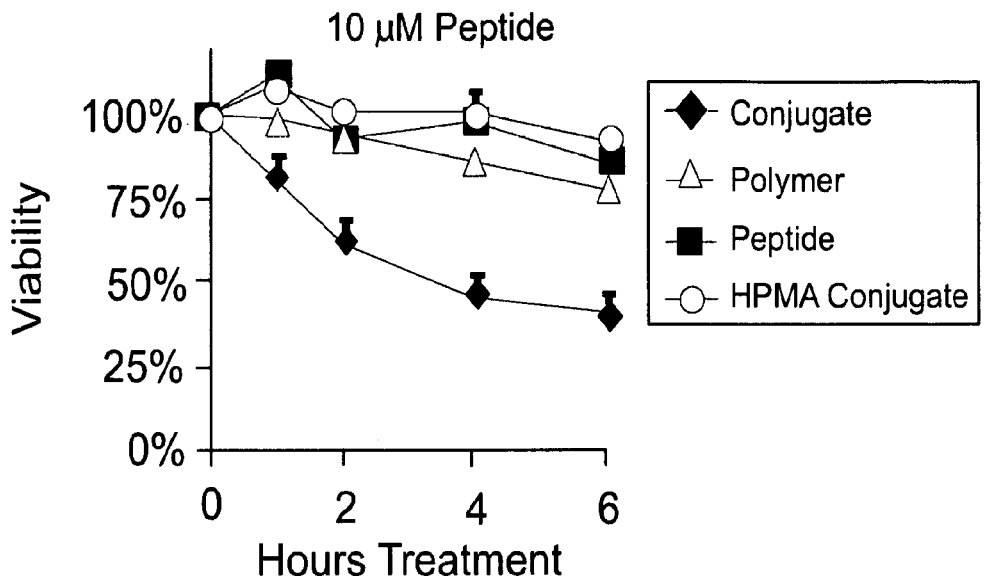
FIGS. 7A and 7B depict the results of a cytotoxity study of a composition according to an embodiment of the present invention.
Figure 7B:
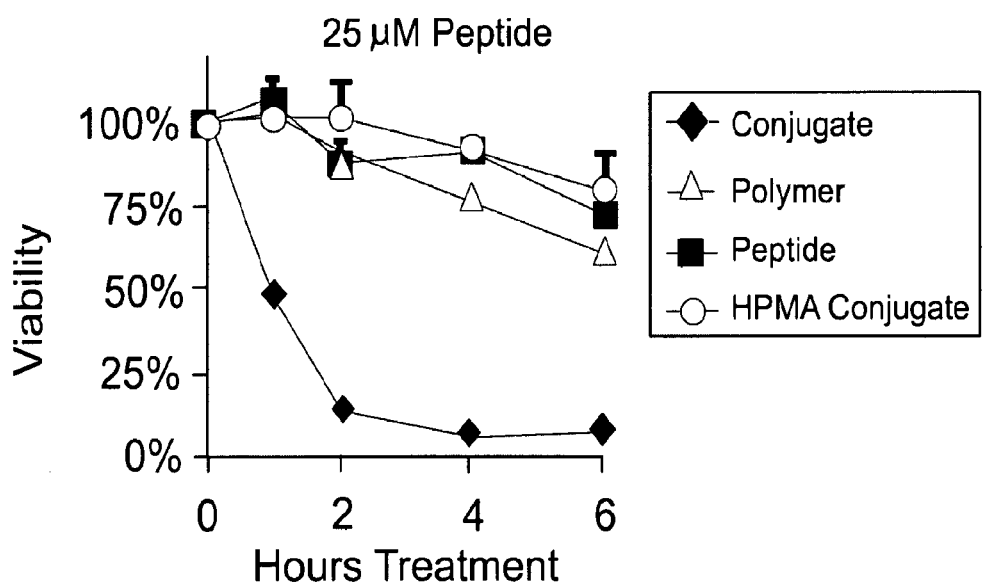

To assess polymer-peptide conjugate bioactivity, a cytotoxicity study was conducted in HeLa cervical cancer cells. The Antp-BH3 polymer conjugate was found to potently trigger HeLa cell death in a dose dependent fashion. Less than 50% HeLa viability was detected after 6 hours of treatment with 10 µM peptide conjugate (FIG. 7A), and samples receiving 25 µM peptide conjugate showed little if any viable cells following as little as 4 hours of exposure (FIG. 7B). Control samples receiving peptide or polymer alone displayed negligible treatment effect, and there was no difference between these control treatment groups. Importantly, Antp-BH3 poly (HPMA) conjugates that lacked the pH-responsive block were similar to both control groups and did not result in significant toxicity, further validating the functionality of the endosomolytic block.

Flow Cytometry Evaluation of Mitochondrial Membrane Potential

Figure 8A:
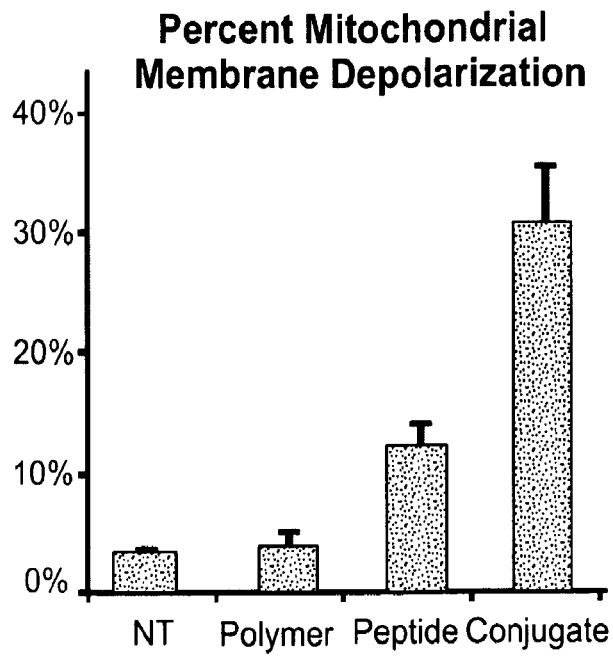
FIGS. 8A and 8B depict the results of a bioactivity study of a composition according to an embodiment of the present invention.

Loss of mitochondrial membrane potential, a known indicator for apoptosis, was assessed using the JC-1 dye. JC-1 exhibits green fluorescence when dispersed in the cytosol, and in healthy cells, it forms red-fluorescent aggregates at the mitochondrial membrane (Cossarizza et al. Biochemical and biophysical research communications. 1993; 197(1):40-45). HeLas were incubated for 2 hours with 10 µM peptide or equivalent conjugate or polymer alone. JC-1 was added at a final concentration of 5 µg/mL and incubated for 15 minutes. Cells were washed 2 times with PBS, trypsinized, and resuspended in 0.5% BSA for flow cytometric analysis. Percent of cells displaying mitochondrial depolarization was quantified based on the number of green fluorescent cells that were negative for red fluorescence. Here, a significant loss of red fluorescent JC-1 aggregates and therefore a loss in mitochondrial polarization was detected following treatment with both the Antp-BH3 peptide and the polymer peptide conjugate (FIG. 8A). Polymer controls were similar to cells receiving no treatment while Antp-BH3 alone and in a polymer conjugate resulted in an approximately 4- and 10-fold increase, respectively, in percent of cells exhibiting loss of mitochondrial polarity.

Caspase 3/7 Activity Assay

Caspase 3/7 activation was measured using a commercially available assay kit. This assay utilizes a profluorescent caspase 3/7 substrate that once enzymatically cleaved becomes fluorescent allowing for determination of relative enzyme activity using a fluorescent plate reader. Here, HeLas were incubated for 30 minutes with 25 μM peptide (alone or as polymer conjugate) in addition to polymer alone in a quantity equivalent to the conjugate samples. Afterwards, a caspase 3/7 fluorigenic indicator was added directly to the culture media for each sample. Plates were shaken for 1 hour and then assayed using a fluorescent plate reader. Data were expressed as percent caspase activity relative to samples receiving no treatment.

Figure 8B:
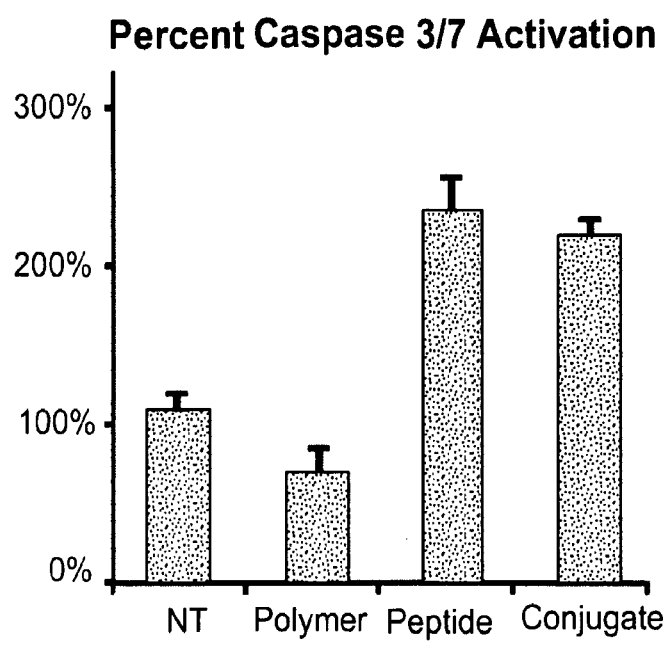

Activation of caspases 3 and 7, which is indicative of pro-apoptotic signaling, can be measured using a profluorescent substrate specific to these proteases. FIG. 8B shows that controls containing the polymer alone displayed equivalent caspase activity relative to negative controls receiving no treatment. However, rapid caspase activation (approximately 2.5-fold) was detected following treatment with the Antp-BH3 peptide by itself or in the polymer conjugate form. The similar effects of Antp-BH3 alone or as a polymer conjugate could indicate that caspase signaling is saturated by treatment with the peptide alone or that other positive feedback mechanisms exist for amplification of perturbations in caspase activation state. Minimally, these results suggest that there was no steric hindrance or other reductions in peptide-induced caspase activity as a result of conjugation to the polymer.

2. The composition of claim 1, wherein the first affinity reagent and the second affinity reagent are included in a single polypeptide chain.

3. A composition for delivering an agent to a cell, comprising:
a bispecific affinity reagent, comprising a first affinity reagent covalently linked to a second affinity reagent, wherein the first affinity reagent binds to a molecule on the surface of a cell, and the second affinity reagent binds to an intracellular target, and
wherein the first affinity reagent is an antibody, antibody fragment, antibody-like molecule, a single protein, peptide, oligosaccharide, or aptamer; and
a pH-responsive, membrane destabilizing polymer.

4. The composition of claim 3 wherein the first affinity reagent is a small molecule selected from the group consisting of folate or a ligand for the asialoglycoprotein receptor.

5. The composition of claim 3, wherein the peptide is an RGD peptide.

6. The composition of claim 1, wherein the first affinity reagent comprises a protein transduction domain.

7. The composition of claim 6, wherein the protein transduction domain comprises antennapedia, TAT, VP22, transportan, penetratin, polyarginine, fragments thereof, or combinations thereof.

The invention claimed is:

1. A composition for delivering an agent to a cell, comprising:
a bispecific affinity reagent, comprising a first affinity reagent covalently linked to a second affinity reagent, wherein the first affinity reagent binds to a molecule on the surface of a cell, and the second affinity reagent binds to an intracellular target, and
wherein the bispecific affinity reagent comprises an antibody, antibody fragment, antibody-like molecule, a single protein, or a specific scFv; and
a pH-responsive, membrane destabilizing polymer.

8. A composition for delivering an agent to a cell, comprising:
a bispecific affinity reagent, comprising a first affinity reagent covalently linked to a second affinity reagent, wherein the first affinity reagent binds to a molecule on the surface of a cell, and the second affinity reagent binds to an intracellular target, and
wherein the second affinity reagent is an antibody, antibody fragment, antibody-like molecule, peptide, or aptamer; and
a pH-responsive, membrane destabilizing polymer.

9. The composition of claim 8, wherein the peptide is BH3 or BAK-BH3.

10. A composition for delivering an agent to a cell, comprising:
- a bispecific affinity reagent, comprising a first affinity reagent covalently linked to a second affinity reagent, wherein the first affinity reagent binds to a molecule on the surface of a cell, and the second affinity reagent binds to an intracellular target, and
- wherein the intracellular target is a DNA binding protein, a cytoplasmic domain of a membrane receptor, a kinase, a GTPase, a phosphatase, or a protein in the Bcl family of proteins; and
- a pH-responsive, membrane destabilizing polymer.

11. The composition of claim 10, wherein the DNA binding protein is p53.

12. The composition of claim 10, wherein the GTPase is ras.

13. The composition of claim 10, wherein the polymer is a copolymer comprising:
- a membrane destabilizing segment comprising a plurality of anionic species that are anionic at about neutral pH, and a plurality of hydrophobic species, and, optionally a plurality of cationic species that are cationic at about neutral pH.

14. The composition of claim 13, wherein the copolymer further comprises:
- an amphiphilic or hydrophilic segment.

15. A composition for delivering an agent to a cell, comprising:
- a bispecific affinity reagent, comprising a first affinity reagent covalently linked to a second affinity reagent through a cleavable linker, wherein the first affinity reagent binds to a molecule on the surface of a cell, and the second affinity reagent binds to an intracellular target, and
- a pH-responsive, membrane destabilizing polymer.

16. A composition for delivering an agent to a cell, comprising:
- a bispecific affinity reagent, comprising a first affinity reagent covalently linked to a second affinity reagent, wherein the first affinity reagent binds to a molecule on the surface of a cell, and the second affinity reagent binds to an intracellular target, and
- a pH-responsive, membrane destabilizing polymer, wherein the pH-responsive, membrane destabilizing polymer comprises a plurality of pendant linking groups, wherein the first affinity reagent is linked to the polymer and wherein the second affinity reagent is linked to the polymer.

17. The composition of claim 16, wherein the first affinity reagent is linked to an end group of the polymer.

18. The composition of claim 16, wherein the second affinity reagent is linked to one of the plurality of pendant linking groups.

19. The composition of claim 16, further comprising a plurality of second affinity reagents, wherein the plurality of second affinity reagents is linked to the polymer via the pendant linking groups.

20. The composition of claim 16, further comprising a plurality of first affinity reagents, wherein the plurality of first affinity reagents is linked to the polymer via the pendant linking groups.

21. The composition of claim 1, further comprising a therapeutic or diagnostic agent.

22. The composition claim 16, wherein the second affinity reagent is cleavably linked to the polymer.

23. The composition of claim 16, wherein the second affinity reagent is an antibody, antibody fragment, antibody-like molecule, or peptide.

* * * * *